(12) United States Patent
Frigg et al.

(10) Patent No.: US 10,641,844 B2
(45) Date of Patent: *May 5, 2020

(54) SIMULATED BONE OR TISSUE MANIPULATION

(71) Applicant: DePuy Synthes Products, Inc., Raynham, MA (US)

(72) Inventors: Robert Frigg, Bettlach (CH); Stuart Weikel, Austin, TX (US); Stefan Schwer, Loerrach (DE); Geoffrey Flexner, Chester Springs, PA (US); Ross Jonathan Hamel, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/908,764

(22) Filed: Feb. 28, 2018

(65) Prior Publication Data

US 2018/0203079 A1  Jul. 19, 2018

Related U.S. Application Data

(63) Continuation of application No. 14/743,895, filed on Jun. 18, 2015, now Pat. No. 10,048,330, which is a (Continued)

(51) Int. Cl.
*G01R 33/28* (2006.01)
*A61B 90/00* (2016.01)
(Continued)

(52) U.S. Cl.
CPC .......... *G01R 33/285* (2013.01); *A61B 5/055* (2013.01); *A61B 5/4836* (2013.01);
(Continued)

(58) Field of Classification Search
CPC .......... A61B 19/54; A61B 17/88; A61B 8/52; A61B 8/0841; A61B 6/032; A61B 5/7405;
(Continued)

(56) References Cited

U.S. PATENT DOCUMENTS 5,682,886 A * 11/1997 Delp .................... A61B 17/154
128/920
6,498,944 B1 * 12/2002 Ben-Haim ........... A61B 5/0215
600/407

(Continued)

*Primary Examiner* — Angela M Hoffa
*Assistant Examiner* — Helene Bor
(74) *Attorney, Agent, or Firm* — Fay Kaplun & Marcin, LLP

(57) ABSTRACT

The present invention is directed to a system and method for performing tissue, preferably bone tissue manipulation. The system and method may include implanting markers on opposite sides of a bone, fractured bone or tissue to facilitate bone or tissue manipulation, preferably in-situ closed fracture reduction. The markers are preferably configured to be detected by one or more devices, such as, for example, a detection device so that the detection device can determine the relative relationship of the markers. The markers may also be capable of transmitting and receiving signals. An image may be captured of the bone or tissue and the attached markers. From the captured image, the orientation of each marker relative to the bone fragment may be determined. Next, the captured image may be manipulated in a virtual or simulated environment until a desired restored orientation has been achieved. The orientation of the markers in the desired restored orientation may then be determined. The desired relationship between markers may then be programmed into, for example, the detection device. Next, actual physical reduction and/or manipulation of the bone may begin. During the manipulation procedure, the orientation of the markers may be continuously monitored and (Continued)

when the markers substantially align with the virtual or simulated orientation of the markers in the desired restored orientation, an indicator signal is transmitted.

9 Claims, 22 Drawing Sheets

Related U.S. Application Data continuation of application No. 14/032,195, filed on Sep. 19, 2013, now Pat. No. 9,921,276, which is a continuation of application No. 11/838,093, filed on Aug. 13, 2007, now Pat. No. 8,565,853.

(60) Provisional application No. 60/837,193, filed on Aug. 11, 2006.

(51) Int. Cl.

| | |
|---|---|
| *A61B 34/20* | (2016.01) |
| *G16H 50/50* | (2018.01) |
| *A61B 5/055* | (2006.01) |
| *A61B 5/00* | (2006.01) |
| *A61B 6/03* | (2006.01) |
| *A61B 6/00* | (2006.01) |
| *A61B 8/08* | (2006.01) |
| *A61B 17/88* | (2006.01) |
| *A61C 19/04* | (2006.01) |
| *G01R 33/56* | (2006.01) |
| *A61B 34/10* | (2016.01) |

(52) U.S. Cl.
CPC .......... *A61B 5/7405* (2013.01); *A61B 6/032* (2013.01); *A61B 6/52* (2013.01); *A61B 8/0841* (2013.01); *A61B 8/52* (2013.01); *A61B 17/88* (2013.01); *A61B 34/20* (2016.02); *A61B 90/36* (2016.02); *A61B 90/39* (2016.02); *A61C 19/04* (2013.01); *G01R 33/5608* (2013.01); *G16H 50/50* (2018.01); *A61B 34/10* (2016.02); *A61B 2034/2063* (2016.02); *A61B 2090/374* (2016.02); *A61B 2090/3762* (2016.02); *A61B 2090/3912* (2016.02); *A61B 2090/3929* (2016.02); *A61B 2090/3958* (2016.02); *A61B 2090/3966* (2016.02); *A61B 2090/3983* (2016.02); *A61B 2090/3987* (2016.02)

(58) Field of Classification Search
CPC ......... A61B 5/4836; A61B 5/055; A61B 6/52; A61B 90/36; A61B 19/5244; A61B 90/39; A61B 2090/3975; A61B 2090/3929; A61B 2090/3995; A61B 2090/3945; A61B 17/66; G01R 33/285; G01R 33/5608; A61C 19/04; G09F 19/3437
See application file for complete search history.

(56) References Cited

U.S. PATENT DOCUMENTS

| | | | |
|---|---|---|---|
| 2003/0120150 A1* | 6/2003 | Govari | A61B 5/0031 600/424 |
| 2006/0241388 A1* | 10/2006 | Lavallee | A61B 90/36 600/416 |
| 2007/0043354 A1* | 2/2007 | Koo | A61B 17/6416 606/58 |
| 2007/0208234 A1* | 9/2007 | Bhandarkar | G06T 7/0012 600/300 |
| 2008/0208055 A1* | 8/2008 | Bertram | A61B 90/36 600/443 |

* cited by examiner

FIG. 10 Step 6

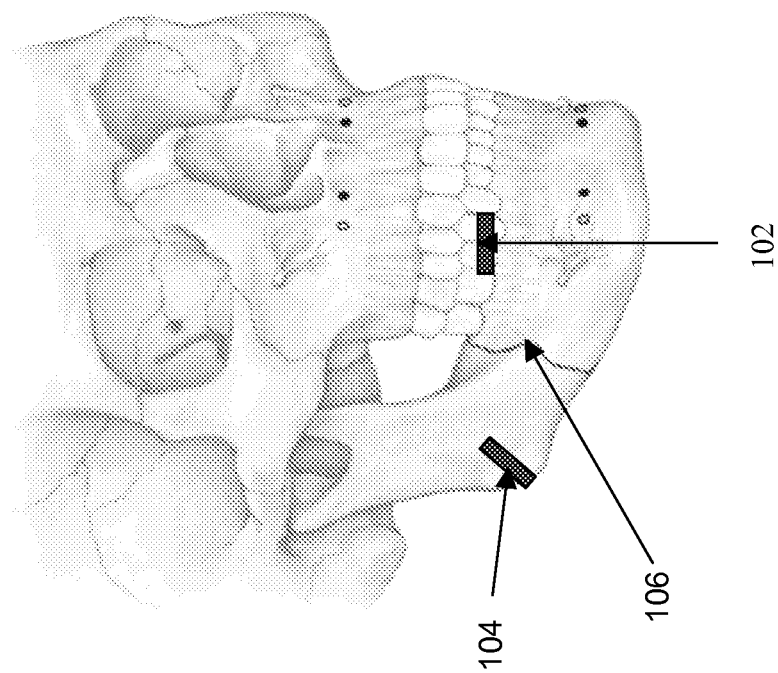
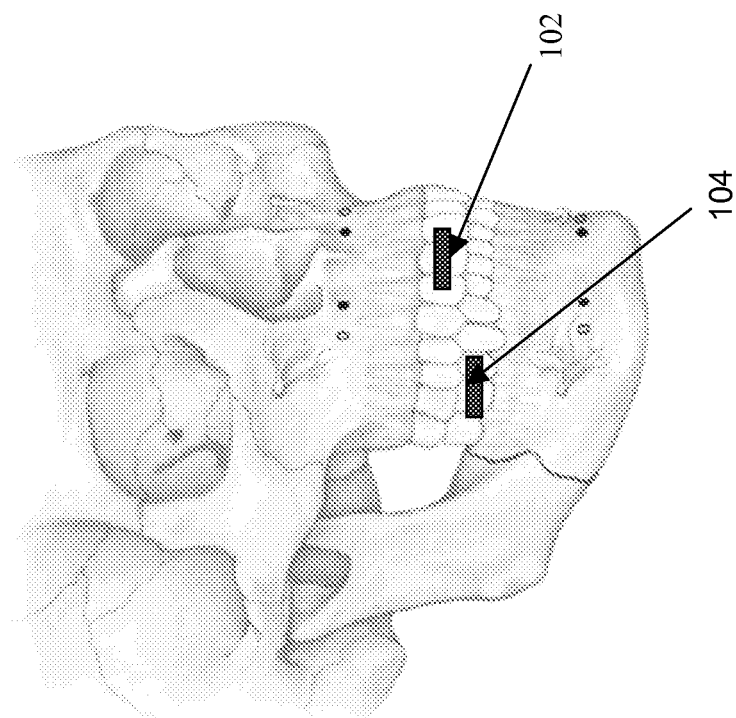
FIG. 20

SIMULATED BONE OR TISSUE MANIPULATION

CROSS REFERENCE TO RELATED APPLICATION

The present application is a Continuation of U.S. patent application Ser. No. 14/743,895 filed Jun. 18, 2015, now U.S. Pat. No. 10,048,330; which is a Continuation of U.S. patent application Ser. No. 14/032,195 filed Sep. 19, 2013, now U.S. Pat. No. 9,921,276; which is Continuation of U.S. patent application Ser. No. 11/838,093 filed Aug. 13, 2007, now U.S. Pat. No. 8,565,853; which claims priority of U.S. Provisional Patent Application Ser. No. 60/837,193 filed Aug. 11, 2006. The entire disclosures of the above patent(s)/application(s) are expressly incorporated herein by reference.

FIELD OF THE INVENTION

The invention relates generally to orthopedics. More specifically, the invention relates to a system and method of performing bone or tissue manipulation.

BACKGROUND OF THE INVENTION

During an operation for bone fracture fixation, proper reduction (e.g. alignment) of the fracture prior to placement of any fixation devices and/or implants affects restoration of the patient's biomechanical function. Fracture reduction may be the most difficult part of the bone fracture fixation procedure. In addition, as techniques for minimally invasive fracture repair have developed, more surgeons are performing closed fracture reduction (e.g. a procedure for setting a fractured bone without making a skin incision at the fracture site).

Surgeons often use visual information to determine the adequacy of fracture reduction. For instance, in limb fracture correction, surgeons may compare the treated limb's length and rotation to the corresponding uninjured limb, the goal being symmetry and balance. Surgeons may also use x-ray data, particularly intra-operative fluoroscopy, to monitor the position and/or orientation of the bone fragments and determine when adequate reduction is achieved.

Computer navigation systems may also be used to aid surgeons in fracture reduction and fracture fixation. Using infrared optical systems and instruments with reflective tracking balls or active infrared light-emitting markers, surgeons can monitor the position and/or orientation of fixation devices and/or implants within the bone and also monitor the position and/or orientation of the bone fragments relative to one another. Other navigation systems utilize electromagnetic fields to accomplish similar objectives. Drawbacks associated with these technologies are the expense and cumbersome nature of the equipment required to use them. Their use in the operating room is particularly challenging because the operating room is generally a very restrictive environment. Operating rooms often lack the necessary space for large equipment and working around the sterile field poses many constraints on freedom to use equipment. For example, with optical navigation systems, the equipment in the operating room is generally large and imposing, and the surgical staff must be mindful of standing in the way of the line-of-sight of the equipment for it to properly function.

Thus, there exists a need for a surgical system and/or method which improves the accuracy of bone or tissue manipulation or bone fracture reduction and enables the surgeon and/or doctor to verify that the desired pre-operative surgical plan for the patient is being achieved.

SUMMARY OF THE INVENTION

The present invention is directed to a system and method for performing tissue, and more specifically bone, manipulation. The system and method seeks to improve the accuracy of bone or tissue manipulation and enable surgeons and/or doctors to verify that the desired pre-operative plan for the patient is being achieved.

In one exemplary embodiment, the method of performing bone or tissue manipulation may include implanting at least one marker on opposite sides of one or more bone, tissue or bone fragments, wherein the position of the markers is preferably capable of being determined. Next, the method may include capturing an image of the bone, tissue or bone fragments with the markers attached. The surgeon and/or doctor may then manipulate the image of the bone, tissue or bone fragments in a virtual or simulated environment to a desired restored orientation. Next, the orientation of the markers in the desired restored orientation is preferably determined. The surgeon and/or doctor may then manipulate the bone, tissue or bone fragments until an indicator signal is generated indicating that the desired restored orientation has been substantially achieved.

In another exemplary embodiment, the method of performing bone or tissue manipulation may include implanting at least one marker on opposite sides of one or more bone, tissue or bone fragments, wherein the position of the markers is preferably capable of being determined. Next, the method may include capturing an image of the bone, tissue or bone fragments with the markers attached. The surgeon and/or doctor may then manipulate the image of the bone, tissue or bone fragments in a virtual or simulated environment to a desired restored orientation. Next, the orientation of the markers in the desired restored orientation may be determined. The method may also include providing an indicator signal when the bone, tissue or bone fragments have been manipulated such that the position of the markers on the bone, tissue or bone fragments substantially corresponds to or matches the position of the markers in the desired restored orientation.

In yet another exemplary embodiment, the method of performing bone or tissue manipulation may include implanting and associating at least one marker on opposite sides of a bone, tissue or bone fragments, wherein the markers are capable of communicating a signal with an external device, the signal containing information as to the markers orientation and/or position. The method may also include acquiring an image of the bone, tissue or bone fragments; manipulating the image of the bone, tissue or bone fragments in a virtual or simulated environment until the bone, tissue or bone fragments have achieved a desired restored orientation; determining the orientation of the markers in the desired restored orientation; programming the external device with the orientation of the markers in the desired restored orientation so that the external device generates an indicator signal when the external device determines that the orientation of the implanted markers substantially corresponds with the position of the imaged markers in the desired restored orientation; and manipulating the bone, tissue or bone fragments until the indicator signal is generated.

The markers may be passive markers. Alternatively, the markers may be capable of one or more of the following: (i)

transmitting a signal to an external device; (ii) receiving a signal from an external device; (iii) both transmitting and receiving a signal; and/or (iv) communicating with one another in order to determine their relative orientation. The markers may also be programmable so that the implanted markers can be programmed before manipulating the bone, tissue or bone fragments, the makers may be programmed with the desired restored orientation.

The method for performing bone or tissue manipulation may also incorporate an external device, the external device being capable of one or more of the following: (i) detecting the positions of the markers; (ii) monitoring the positions of the markers; (iii) both detecting and monitoring the positions of the markers; (iv) communicating with the markers; (v) being programmed with the orientation and/or position of the markers and/or (vi) generating an indicator signal upon determining that the position of the implanted markers have been manipulated so that they substantially correspond with the position of the virtual markers in the desired restored orientation.

The method of performing bone or tissue may further include implanting at least one fracture fixation device to the bone, tissue or bone fragments.

In use, preferably one or more of the steps of implanting the markers, capturing the image of the bone fragments, manipulating the image of the bone fragments, determining the orientation of the markers, and/or manipulating the bone, tissue or bone fragments occurs outside of the operating room setting.

In yet another exemplary embodiment, the system and method of performing bone or tissue manipulation may include implanting markers on opposite sides of a bone, tissue or bone fragments. The position of the markers are preferably capable of being detected by an external device so that the external device can determine the relative relationship of the markers. The markers may be passive or active. If active, the markers may be configured to transmit a signal to and optionally receive a signal from the external device. The markers may also be capable of transmitting and optionally receiving signals with respect to one another. The method of performing bone or tissue manipulation may also include capturing an image of the bone, tissue or bone fragments and optionally the attached markers. From the captured image, the position and/or orientation of each marker relative to the bone, tissue or bone fragments may be determined. Next, the captured image may be manipulated in a virtual or simulated environment until a desired restored orientation has been achieved. The position and/or orientation of the markers in the desired restored orientation may then be determined and/or calculated.

The desired relationship between the markers may preferably be programmed into the markers and/or the external device. Next, physical manipulation of the bone, tissue or bone fragments may begin. During physical manipulation, the position and/or orientation of the markers may be monitored, preferably continuously, so that when the markers substantially align with the computer generated position and/or orientation of the markers in the desired restored orientation, an indicator signal is transmitted.

BRIEF DESCRIPTION OF THE DRAWINGS

The system is explained in even greater detail in the following exemplary drawings. The drawings are merely exemplary to illustrate the structure of preferred devices and certain features that may be used singularly or in combination with other features. The invention should not be limited to the embodiments shown.

FIG. 20 illustrates exemplary marker placements;

DETAILED DESCRIPTION

Figure 1:
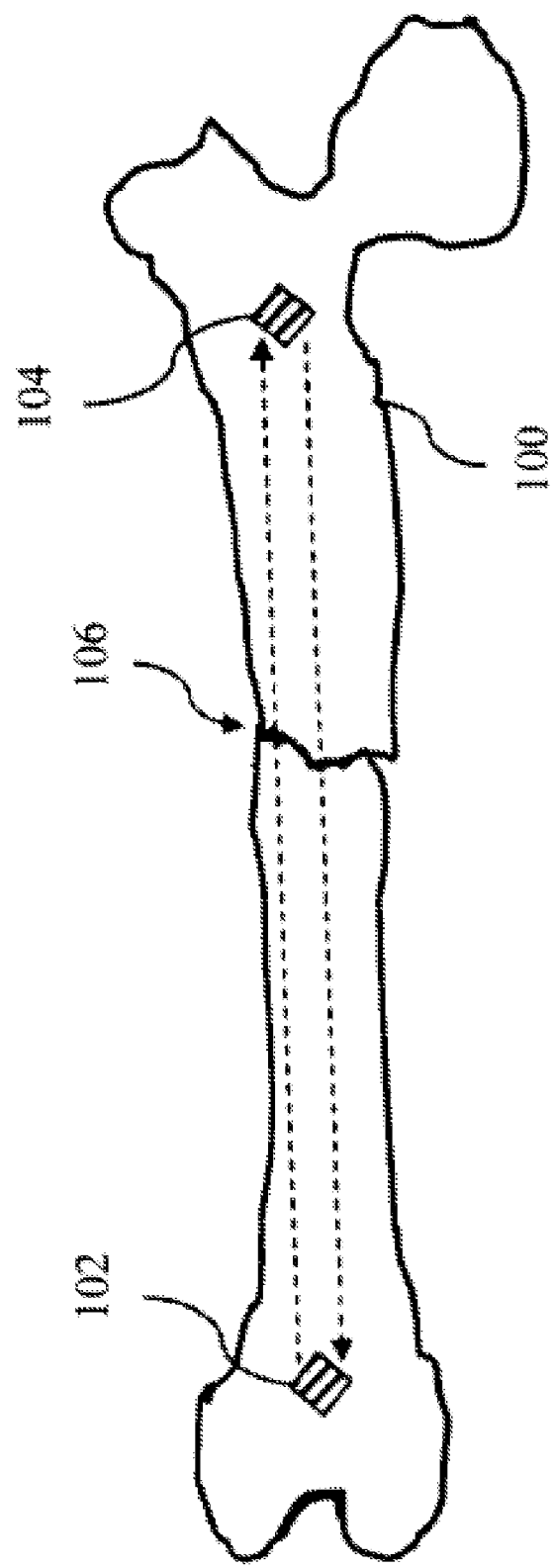
FIG. 1 illustrates a fractured bone to which markers have been attached, FIG. 1 further illustrates a two-way line of communication between the markers.

Certain exemplary embodiments of the invention will now be described with reference to the drawings. In general, such embodiments relate to an apparatus, system and/or method for performing and optionally verifying tissue, preferably bone, manipulation.

While the system and method of the present invention may be generally described as, generally shown as and may generally be used in connection with fracture fixation, it should be understood that the system and/or method for performing bone or tissue manipulation is not limited in use to repairing bone fractures. Rather, the system and/or method for performing bone or tissue manipulation may be used for manipulating bone, manipulating tissue, manipulating bone fragments caused by, for example, injury, deformation, degeneration, disease, etc. The system and/or method for performing bone or tissue manipulation is not limited to any particular type of fracture and, in fact, may be used even where no fracture exists. The system and/or method for bone or tissue manipulation only requires desired relative movement or manipulation of bone, bone fragments, tissue, etc.

The system and/or method for performing bone or tissue manipulation may be used in connection with bone markers. The system and/or method, by way of non-limiting example, may include implanting markers on opposite sides of a fractured bone. The implantation of the markers may be used to facilitate in-situ closed fracture reduction. The system and/or method preferably enables one or more steps of the fracture reduction procedure to occur substantially outside of the operating room setting. For example, preferably one or more of the steps of implanting the markers, capturing the image of the bone fragments, manipulating the image of the bone fragments, determining the orientation of the markers, programming the implanted markers, and/or manipulating the fracture bone may occur outside of the operating room setting.

The markers may be passive (e.g., incapable of transmitting and/or receiving a signal, for example, a radiopaque marker) or active (e.g. a transmitter capable of sending a signal). The markers may incorporate electronic transmitters or receivers. The markers may incorporate both receivers and transmitters so that the markers can receive and transmit a signal. The markers may be capable of receiving and sending signals with an external device, such as, for example, a detection device, which will be described in greater detail below. Alternatively and/or in addition, the markers may be capable of receiving and sending signals with respect to one another in order to determine their relative orientation. The signal preferably contains information as to the position and/or orientation (collectively referred to herein as orientation) of the markers and hence the attached bone fragments. Alternatively, one of the markers may incorporate a transmitter while the other marker may incorporate a receiver. For example, if during a surgical procedure, it is desired for one bone fragment to remain relatively stationary and for the other bone fragment to be manipulated, it may not be necessary for both markers be configured to receive and transmit signals.

Moreover, the markers may be nonprogrammable and the detection device, which will be described in greater detail below, may be programmable such that the detection device is capable of determining when the markers have arrived at the desired restored orientation with respect to the planned fracture reduction, which will also be described in greater detail below. Alternatively and/or in addition, one of the markers may be programmable while the other marker(s) may be nonprogrammable, while in an alternate embodiment, both or all of the markers may be programmable so that the markers themselves are capable of determining when they have arrived at the desired restored orientation. In addition, one of the markers may function in a master mode while the other marker(s) may function in a slave mode.

The markers may also be anchored to the bone by any means known in the art including but not limited to pins, nails, barbs, threads, screws, adhesive, etc. The markers are preferably capable of being fixedly secured with respect to the bone to which they are being attached so that the orientation of the markers with respect to the bone is fixed. The markers preferably are small enough so that they may be inserted into the patient's body and attached to a patient's bone through a small incision, such as for example a stab incision. Alternatively, the markers may be inserted into the patient's body by any means including but not limited to, an open incision, an injection, etc.

A function of the markers is that the position of the marker should be detectable. It should be understood that the system and/or method for performing bone or tissue manipulation is not limited in use to any particular type of marker.

In use, the position of the markers may be detected by any means known in the art including but not limited to the detection device. The detection device may detect the position of the markers by any means known in the art including, but not limited to, visual, sound, radio waves, infrared, electromagnetic, electrical, x-rays, reflective, ultrasound, mechanical waves, GPS systems or chips, magnetic, transducer, etc. In addition, as previously mentioned, the markers may be capable of sending a signal to the detection device and the detection device may determine the relative relationship of the markers.

The detection device may also be capable of generating and transmitting an indicator signal when the desired restored orientation of the fractured bone has been achieved, as will be described in greater detail below. Alternatively, an indicator device which may be a separate and distinct device from the detection device may generate and transmit an indicator signal when the desired restored orientation of the tissue, bone or bone fragments has been achieved.

The detection device can be any known device capable of detecting the position of the markers. For example, the detection device may be a computer console, x-ray machine, computed tomography (CT) scan, a receiver specifically designed for such purpose, etc. It should be understood that the system and/or method for performing bone or tissue manipulation is not limited in use to any particular type of detection device.

Figure 2:
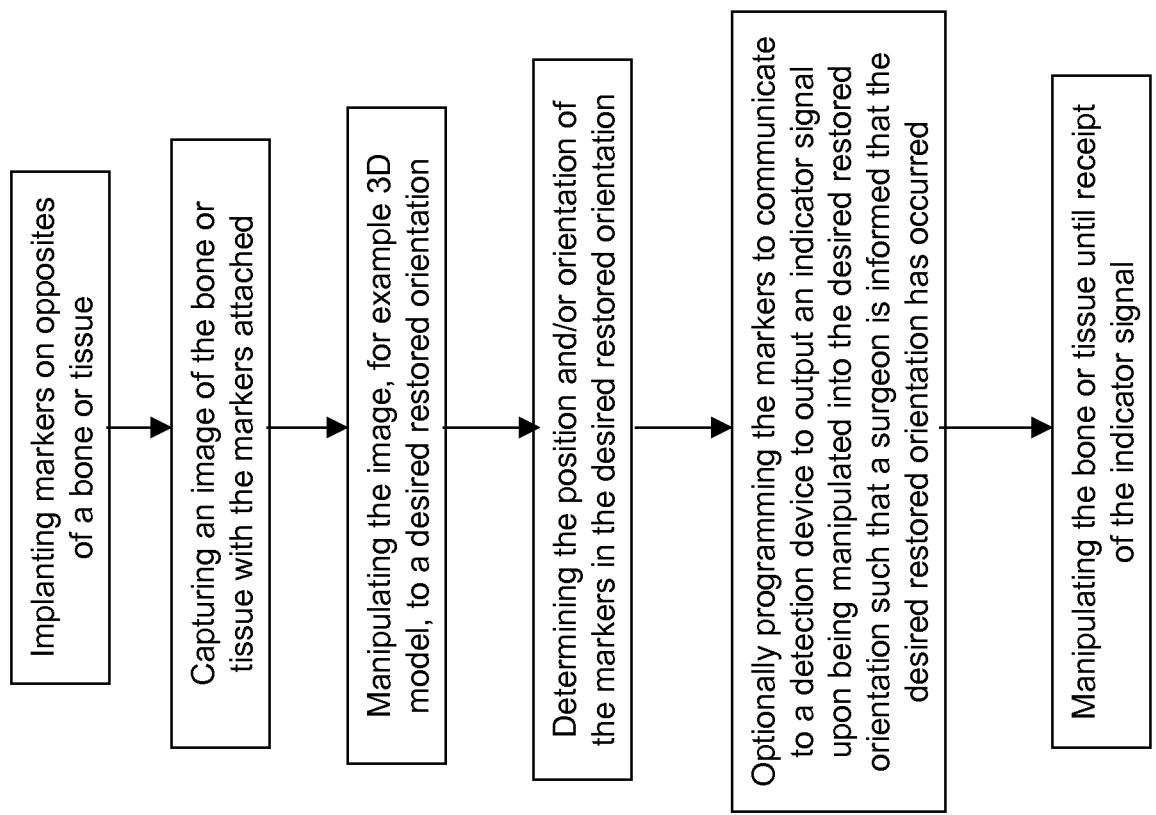
FIG. 2 illustrates a flow chart describing an exemplary method for performing bone or tissue manipulation.

Referring to FIGS. 1 and 2, an exemplary system and/or method for performing bone or tissue manipulation will be described in connection with a mid-shaft fracture of a long bone 100. As shown, the surgeon and/or doctor preferably places a single marker 102, 104 on each side of the fracture 106. Although more than one marker may be placed on either side of the fracture if desired and/or required. The markers 102, 104 are preferably positioned in locations that will not interfere with any surgical instruments that may be required to complete the fracture reduction. Moreover, the markers 102, 104 are preferably positioned in locations that will not interfere with placement of any fixation devices and/or implants that may be implanted. More preferably, the markers 102, 104 are preferably secured to the fractured bone on either side of the fracture 106 as close as possible to the bone ends opposite the bone fracture 106. The placement of the markers 102, 104 preferably occurs prior to the fracture fixation surgery so that the placement of the markers 102, 104 may occur outside of the operating room, in advance of the surgeon's pre-operative planning. For example, a radiologist may implant the markers 102, 104 prior to image acquisition.

Next, a scan may be taken of the fractured bone 100 and markers 102, 106. The scan may be any scan known in the art including but not limited to a computed tomography (CT) scan, a three dimensional (3D) image capture, a set of at least two non-parallel two dimensional (2D) images, which allows for 3D reconstruction of the image data, etc.

Next, using the captured image, the orientation of each marker 102, 104 relative to the bone fragment to which it is attached may be determined. The markers 102, 104 may essentially serve as a surgeon-applied landmark. As part of the pre-operative planning, the surgeon can manipulate the captured image or software-generated model, preferably 3D solid model, of the bone fragments in a simulated or virtual environment until a desired restored orientation has been achieved.

Many navigational system manufacturers produce and/or sell software capable of the desired functionality. For example, software currently exists for navigating IM nailing. Moreover, off-the-shelf software packages containing similar functionality include BrainLAB Trauma Module, Sekvenca.com and Singapore General Hospital Project. In an alternate exemplary embodiment, instead of working with software generated 3D solid models, actual patient data or an actual dummy model prepared using the patient's data may be utilized. It should be understood that the system and/or method for performing bone or tissue manipulation is not limited in use to any particular type of navigational device and/or software.

Once the desired restored orientation has been achieved by manipulating the simulated or virtual image, the orientation of the markers 102, 104 in their new, desired restored orientation may be determined and/or calculated. The desired restored orientation of the markers 102, 104 may then be programmed into the detection device. Alternatively and/or in addition, if the markers 102, 104 are capable of receiving and transmitting a signal, the desired restored orientation of the markers 102, 104 may be programmed into the markers 102, 104 themselves.

Once the desired restored orientation of the markers 102, 104 has been programmed into, for example, the detection device, actual physical reduction of the fracture may begin. The actual physical reduction of the fracture may be performed by any means including but not limited to surgeon applied distractive forces via a reduction frame, fracture table, etc. During actual physical reduction of the fracture, the orientation of the markers 102, 104 may be monitored, preferably continuously, by, for example, the detection device. Alternatively and/or in addition, the markers 102, 104 may signal to one another their relative orientation. The markers 102, 104 may communicate with one another and/or with the detection device by any means including, but not limited to, via hard wire, wirelessly such as by radio frequency or other electromagnetic signals, via acoustic signals, etc.

Once the detection device and/or the markers 102, 104 have detected that the orientation of the markers 102, 104 substantially corresponds with or substantially matches, within some acceptable tolerance, the orientation of the markers in the desired restored orientation of the image from the virtual or simulated environment, an indicator signal is preferably generated and transmitted to indicate that the desired restored orientation has been achieved. Once the indicator signal has been generated, the fixation procedure may proceed as is normally performed in order to fix the relative orientation of the bone fragments. The orientation of the bone fragments may be fixed by any means known in the art including, but not limited to, a plate and screw construct, a rod and screw construct, external fixator, IM rod, etc.

The indicator signal may be any indicator signal known in the art including, but not limited to, visual cues such as, for example, color changes or alignment of articulating lines on a computer screen, sounds, flashes of light, etc. The indicator signal may be generated by the detection device. Alternatively, the indicator signal may be generated by an indicator device specifically designed for such purpose. Alternatively, the indicator signal may be generated by one or more of the markers 102, 104, a marker transponder or receiver (which will be described in greater detail below), etc.

Upon completion of the fracture reduction procedure, the markers 102, 104 may be removed from the patient's body. Alternatively, the markers 102, 104 may be made from a resorbable or partially resorbable material. As will be generally understood by one of ordinary skill in the art, the use of resorbable markers eliminates the need for subsequent surgical removal of the markers 102, 104.

Figure 3:
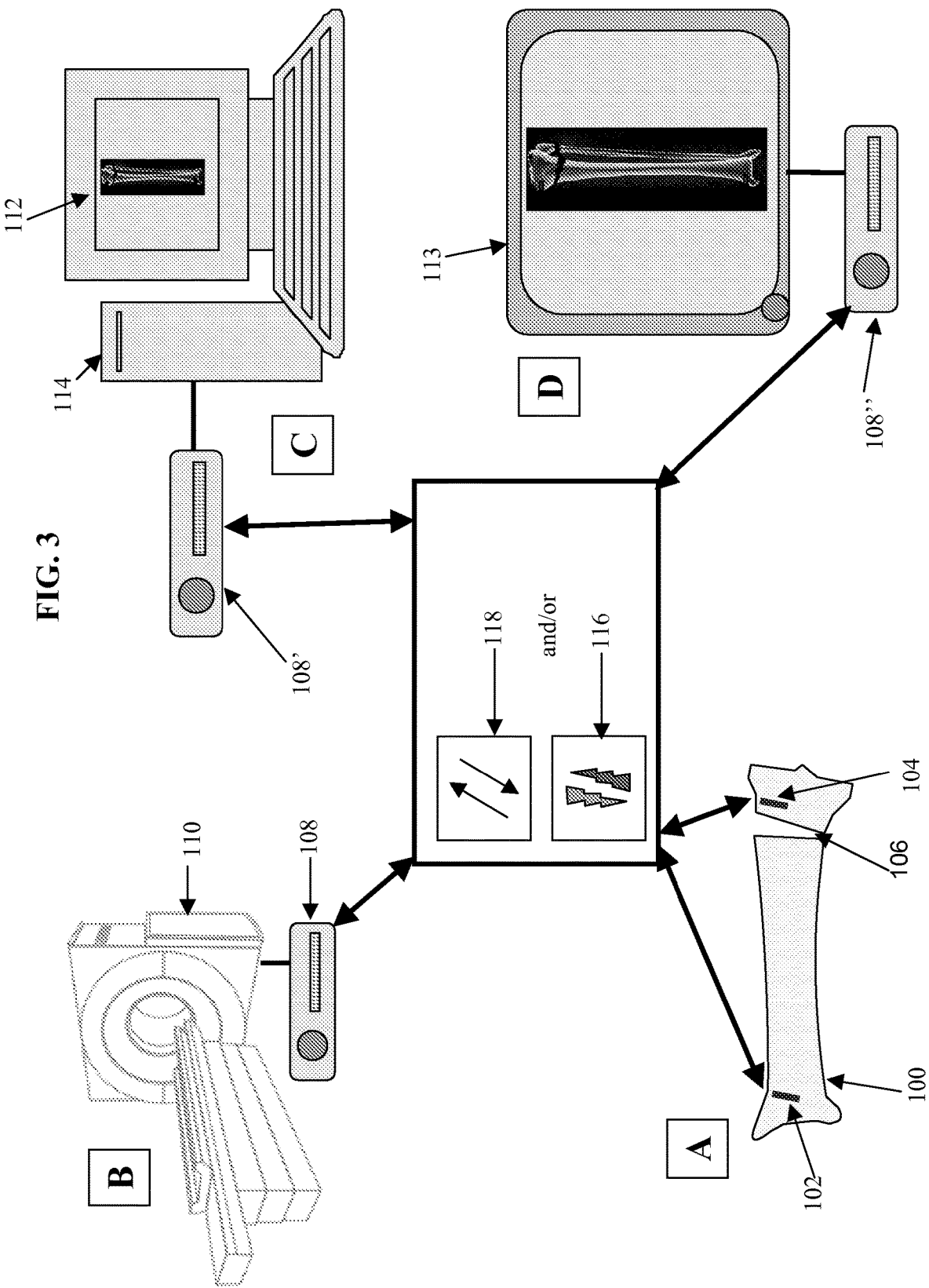
FIG. 3 illustrates an exemplary method for performing bone or tissue manipulation.

Referring to FIG. 3, an exemplary method for performing bone or tissue manipulation may include implanting one or more markers 102, 104 on either side of a fracture 106 of a long bone 100. Next, an image of the fractured bone 100 and markers 102, 104 may be taken using, for example, an x-ray machine 110 or any other suitable imaging device. Imaging data may be provided via a marker transponder or receiver (e.g., a signal receiving and/or transmitting unit) 108 so that the marker transponder or receiver 108 can transmit the data to the detection device 114, which may be optionally connected to another marker transponder or receiver 108' so that the detection device 114 can transmit and/or receive data. Alternatively, the detection device 114 may integrally incorporate the marker transponder or receiver 108'. The image of the fractured bone 100 and bone markers 102, 104 may be displayed on a monitor 112. In addition, the image of the fractured bone 100 may be sent via a marker transponder or receiver 108" to an intra-operative bone and marker monitor 113 so that the image may be viewed in the operating room. As shown, the intra-operative bone and marker monitor 113 may be connected to a marker transponder or receiver 108" so that the intra-operative bone and marker monitor 113 can receive and/or transmit data. Alternatively, the intra-operative bone and marker monitor 113 may integrally incorporate the intra-operative bone and marker monitor 113". As described, the marker transponder or receiver may enable the data to be sent wirelessly. Alternatively, the data may be sent via wire leads 118 or any other methods.

Figure 4:
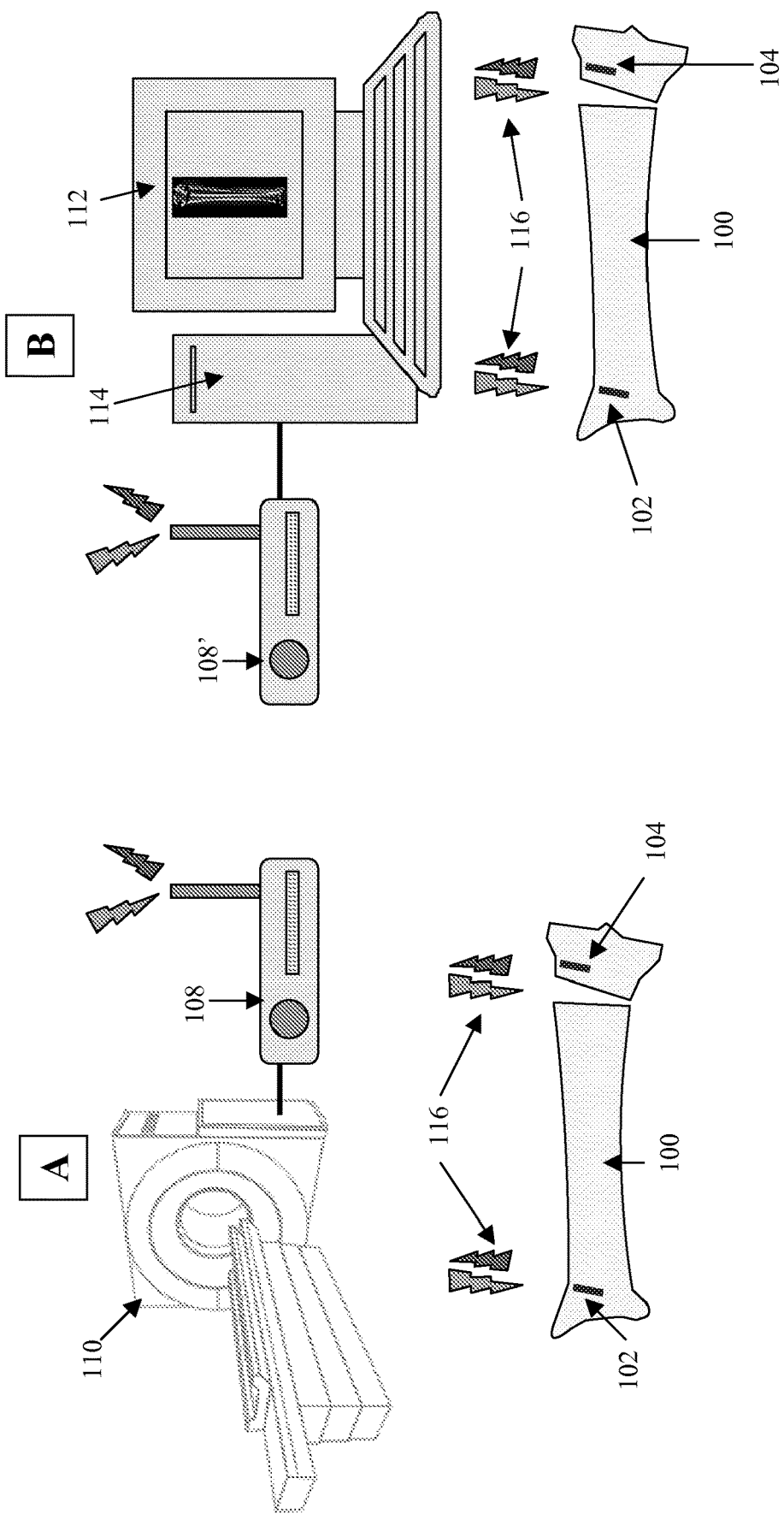
FIG. 4 illustrates two ways in which data may be generated in accordance with the exemplary embodiment of FIG. 3.

As shown in FIG. 4 and as previously mentioned, data relating to the relative orientation of the markers 102, 104, and hence to the fractured bone fragments, may be generated primarily for two reasons. First, data relating to the relative orientation of the markers 102, 104 may be generated in order to acquire images of the fractured bone 100 and to define the orientation of the markers 102, 104 relative to the actual image generated by the x-ray or other similar machine 110. Second, data relating to the relative orientation of the markers 102, 104 may be generated to define the desired orientation of the markers 102, 104 relative to the newly edited image.

Figure 5:
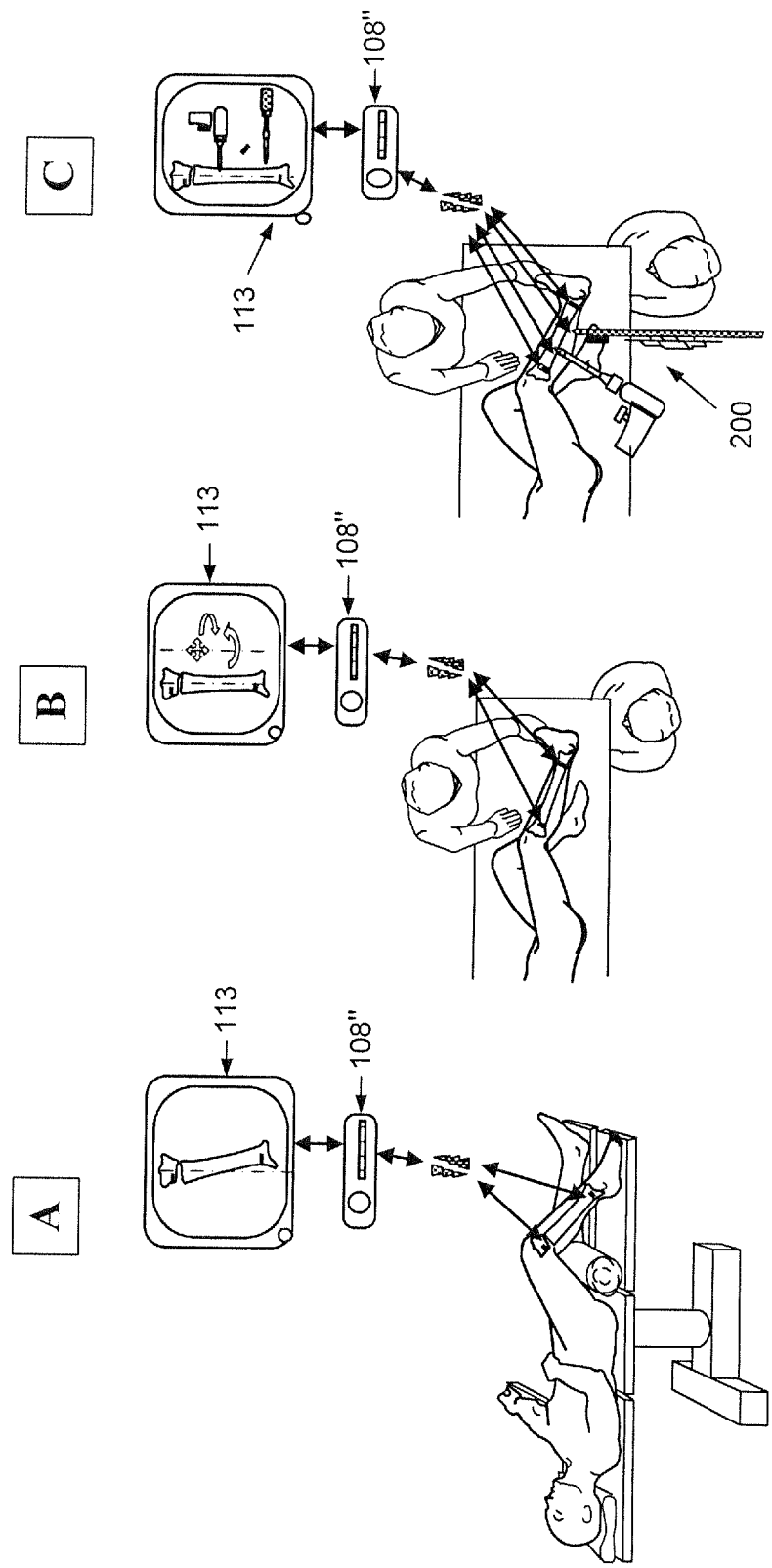
FIG. 5 illustrates three ways in which the acquired data may be used in accordance with the exemplary embodiment of FIG. 3.
Figure 6:
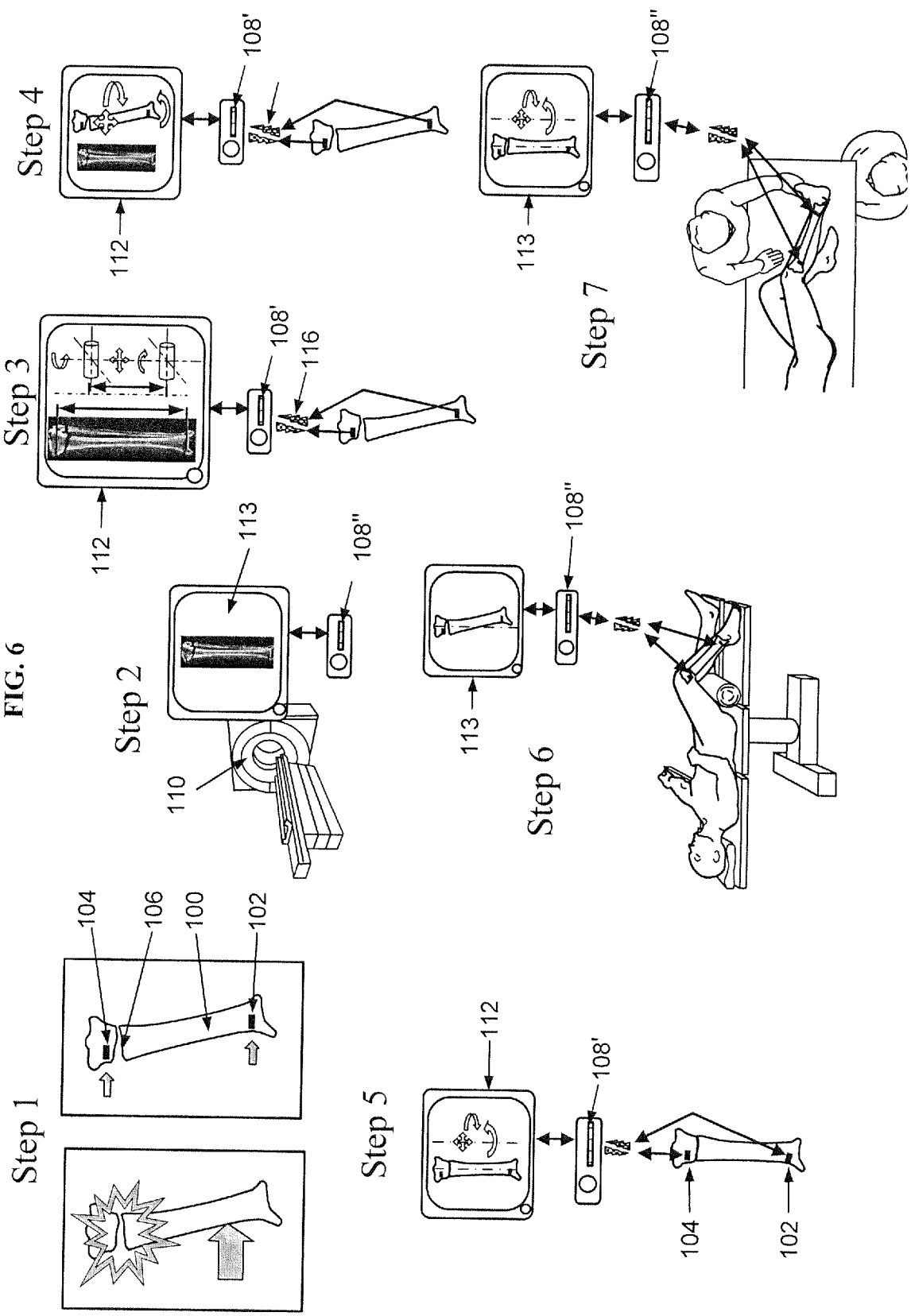
FIG. 6 illustrates an exemplary method for performing bone or tissue manipulation.
Figure 7:
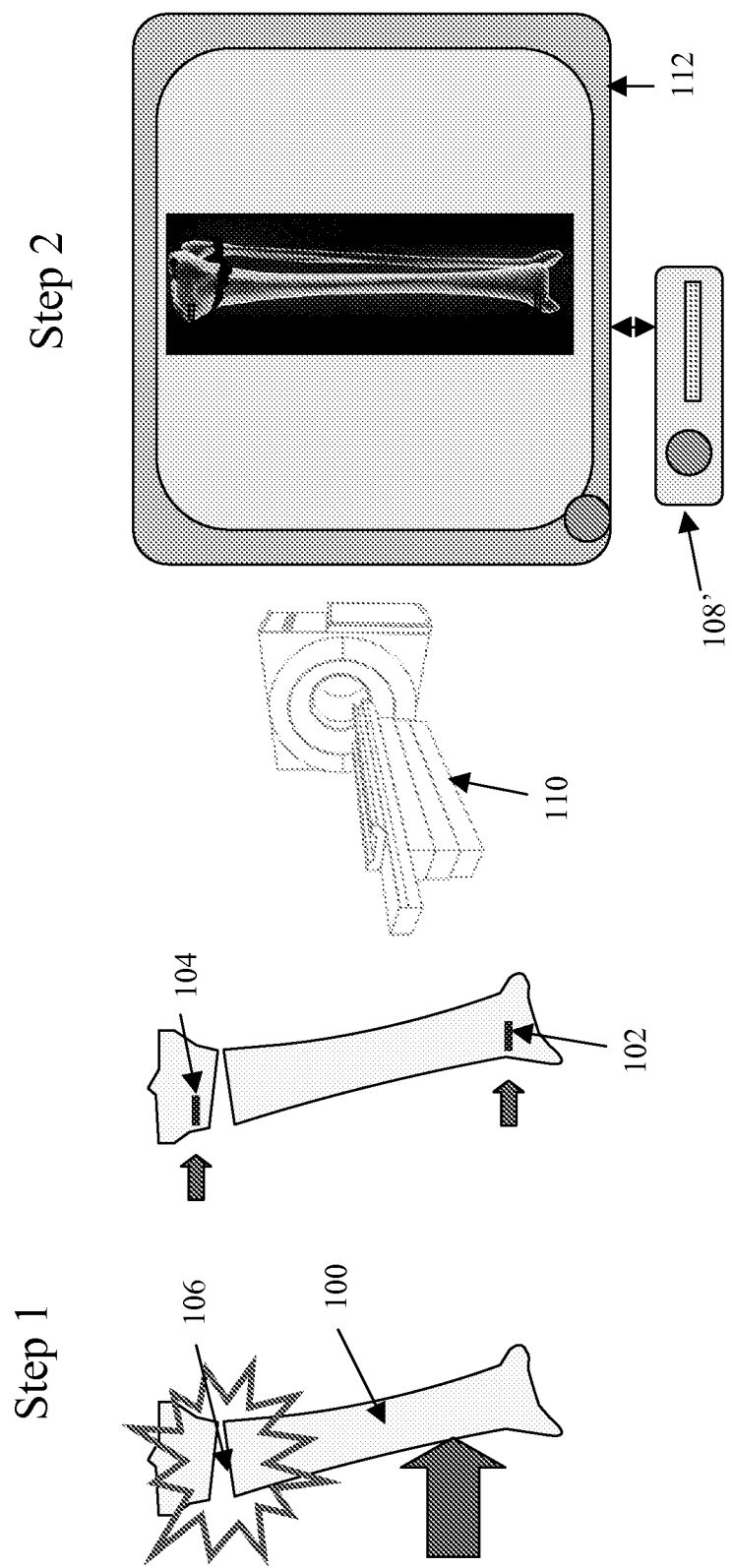
FIG. 7 further illustrates the exemplary method for performing bone or tissue manipulation of FIG. 6.
Figure 8:
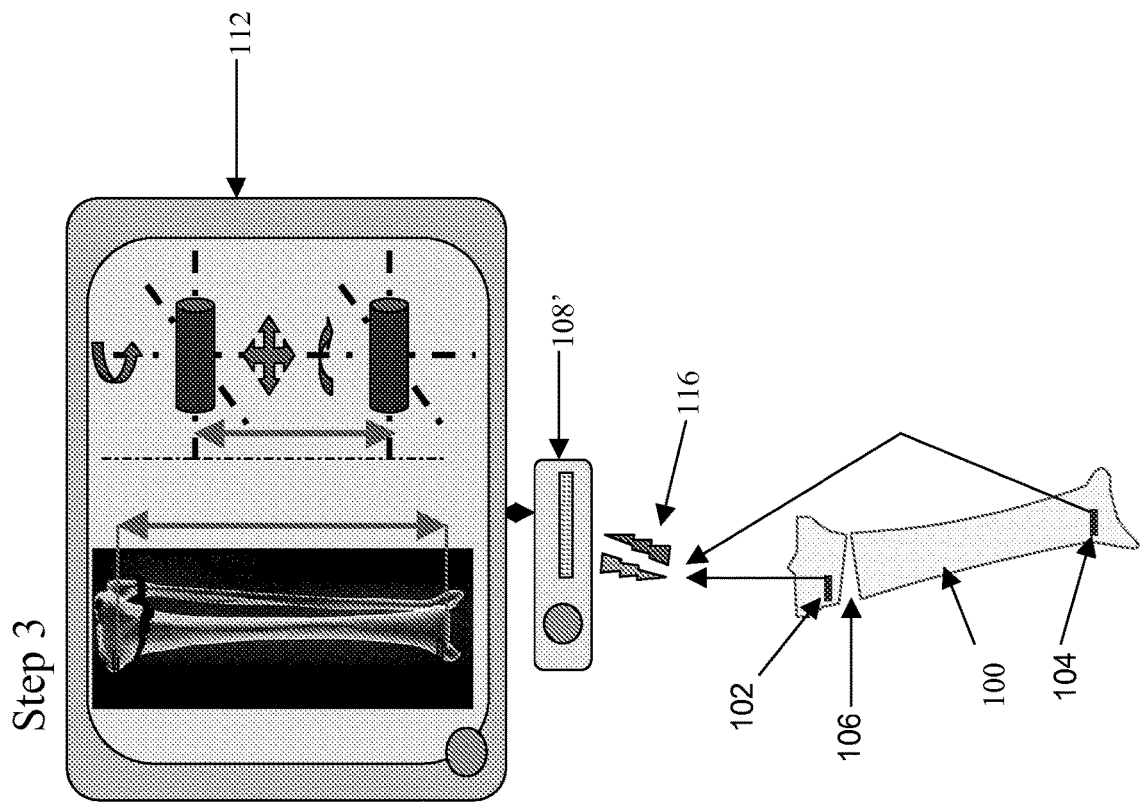
FIG. 8 further illustrates the exemplary method for performing bone or tissue manipulation of FIG. 6.
Figure 9:
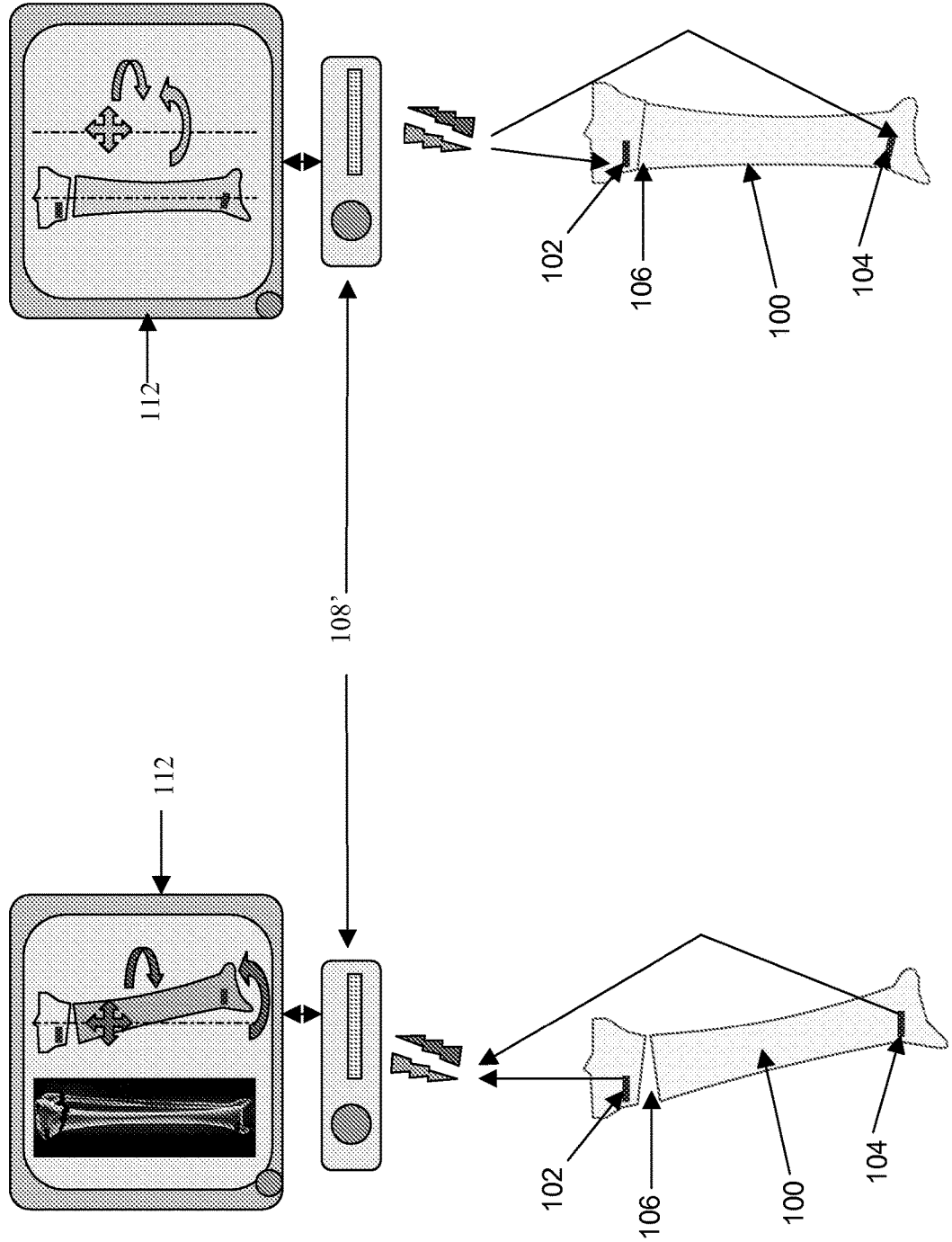
FIG. 9 further illustrates the exemplary method for performing bone or tissue manipulation of FIG. 6.
Figure 10:
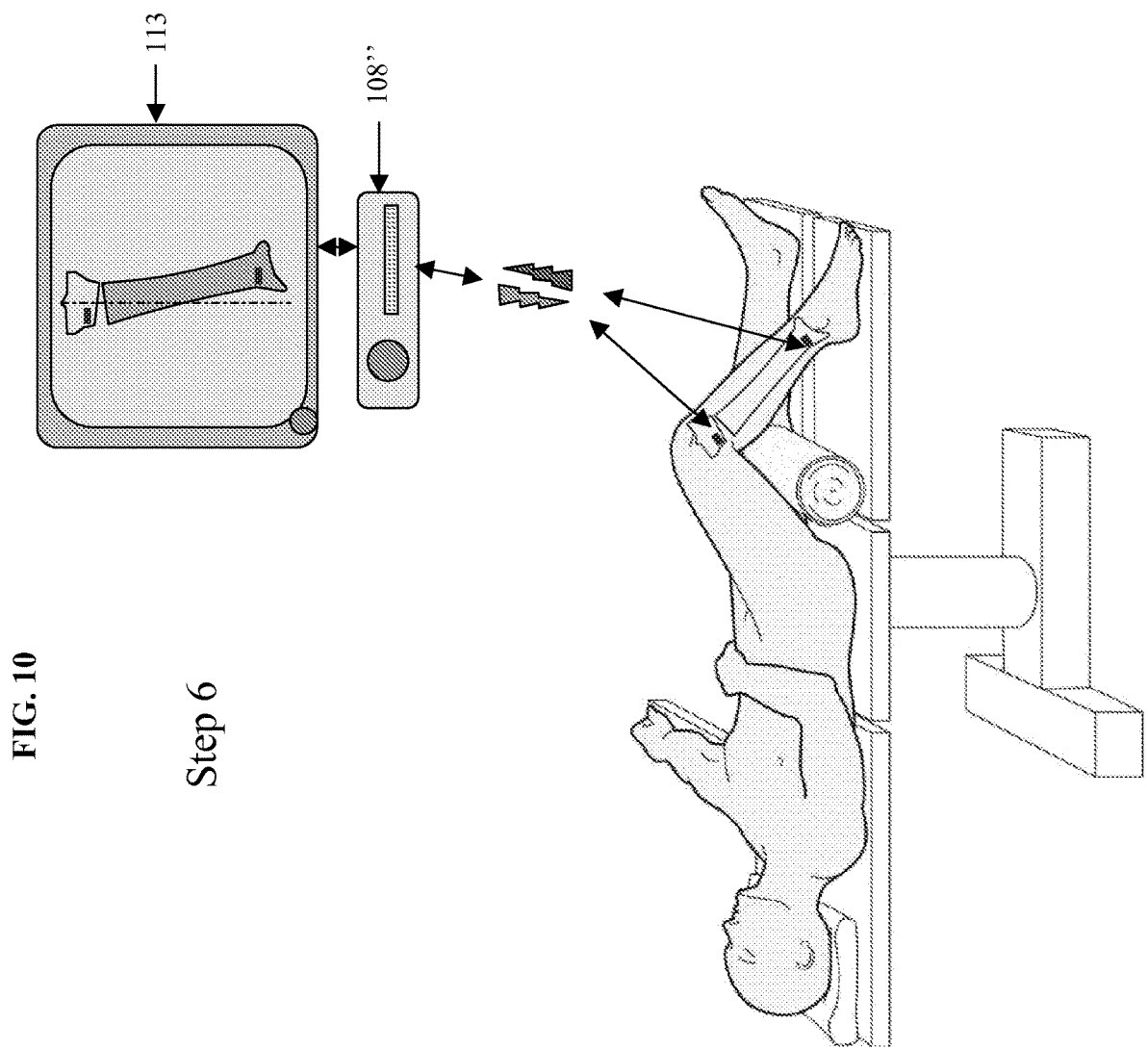
FIG. 10 further illustrates the exemplary method for performing bone or tissue manipulation of FIG. 6.
Figure 11:
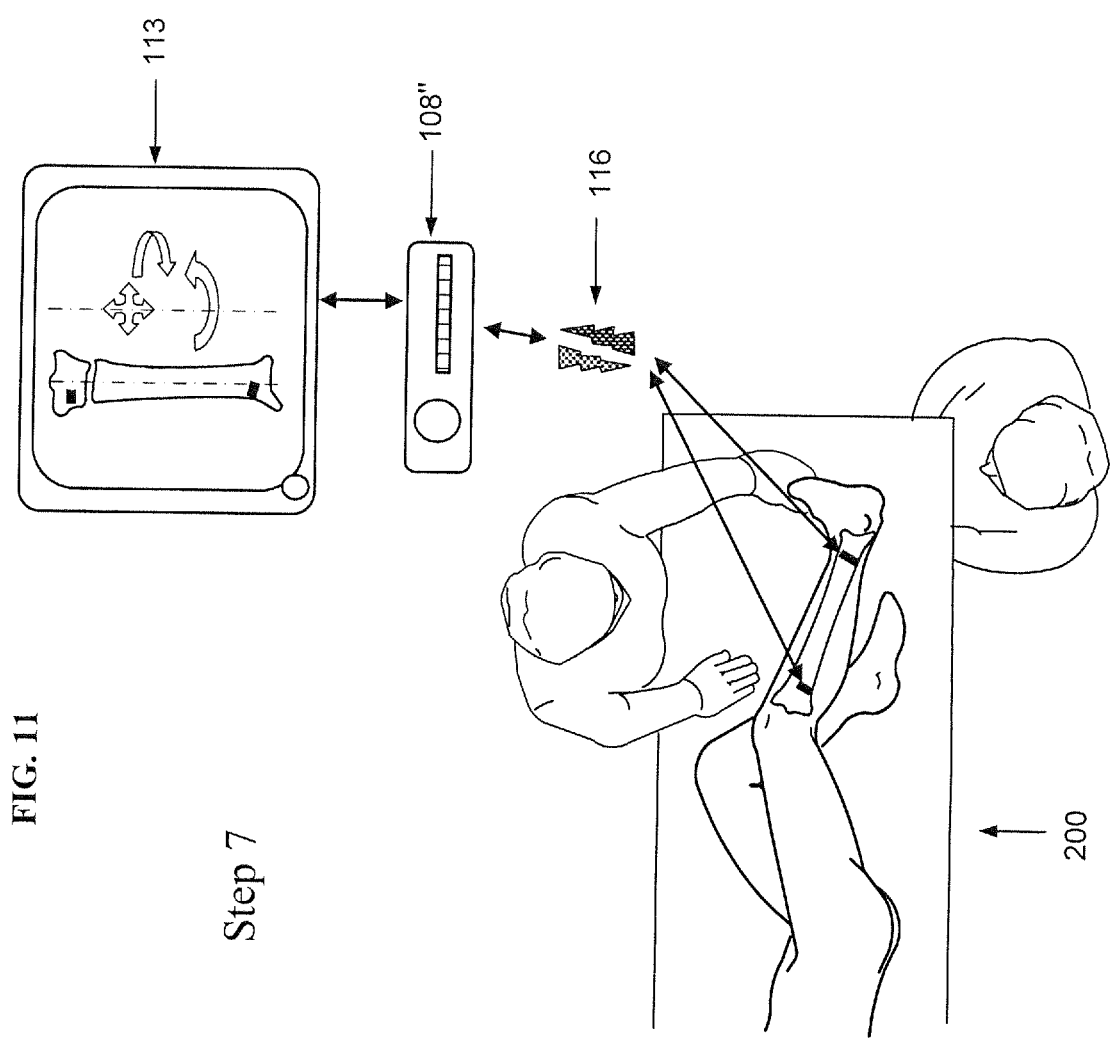
FIG. 11 further illustrates the exemplary method for performing bone or tissue manipulation of FIG. 6.
Figure 12:
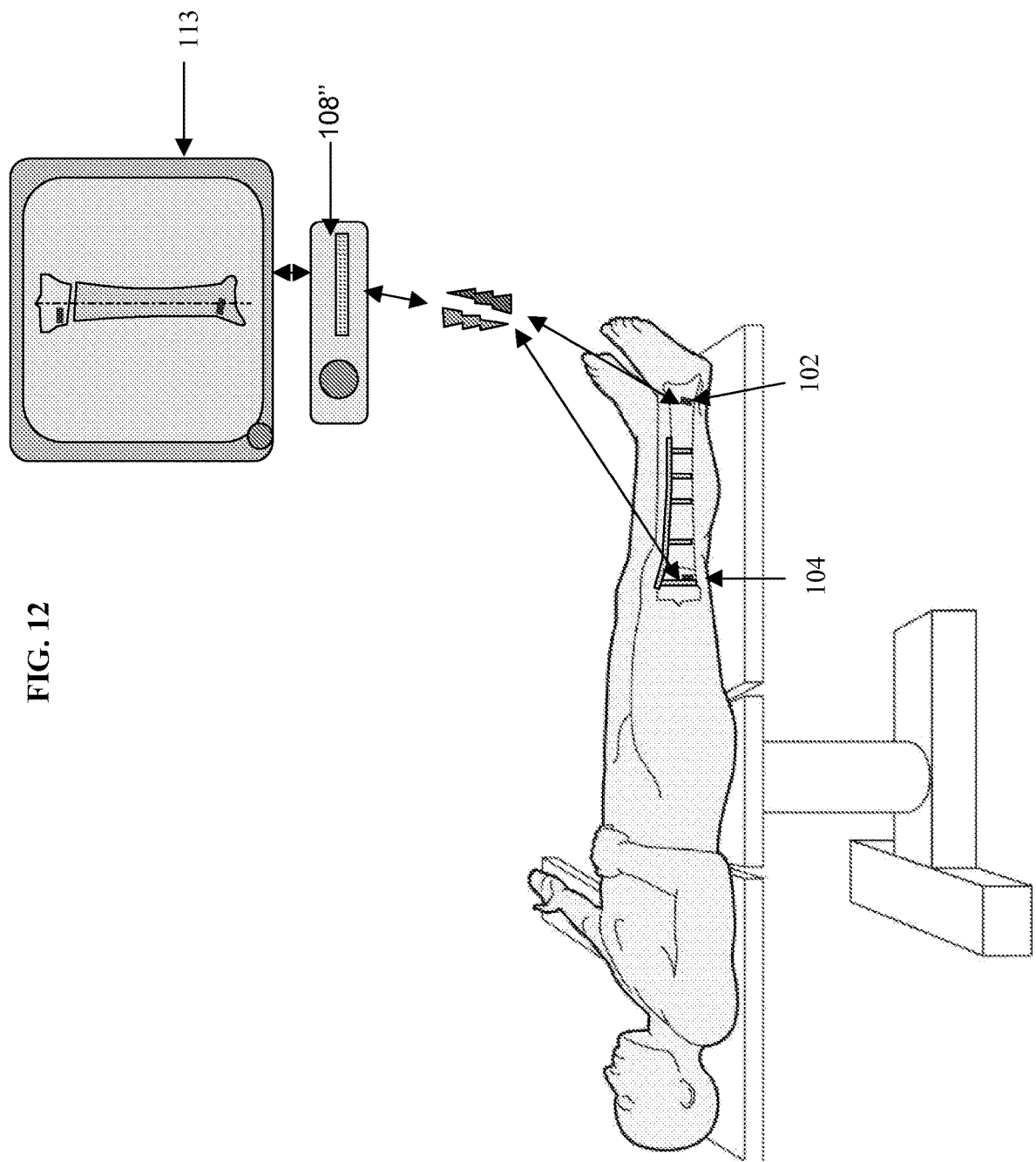
FIG. 12 illustrates the exemplary method for performing bone or tissue manipulation of FIG. 6.

Moreover, as best shown in FIG. 5, the data acquired, as described above, may be used primarily for three reasons. First, the data acquired may be used to intra-operatively monitor and optionally display the attached bone fragments in order to show the doctor and/or surgeon the orientation of the bone fragments during re-alignment. Second, the data acquired may be used to intra-operatively monitor and optionally display the attached bone fragments so that the doctor and/or surgeon can manipulate the bone fragments aided by the system. Third, the data acquired may be used to intra-operatively monitor and optionally display the attached bone fragments so that the doctor and/or surgeon can navigate surgical instruments 200 and/or fixation devices/implants (as will be described in greater detail below).

Figure 18:
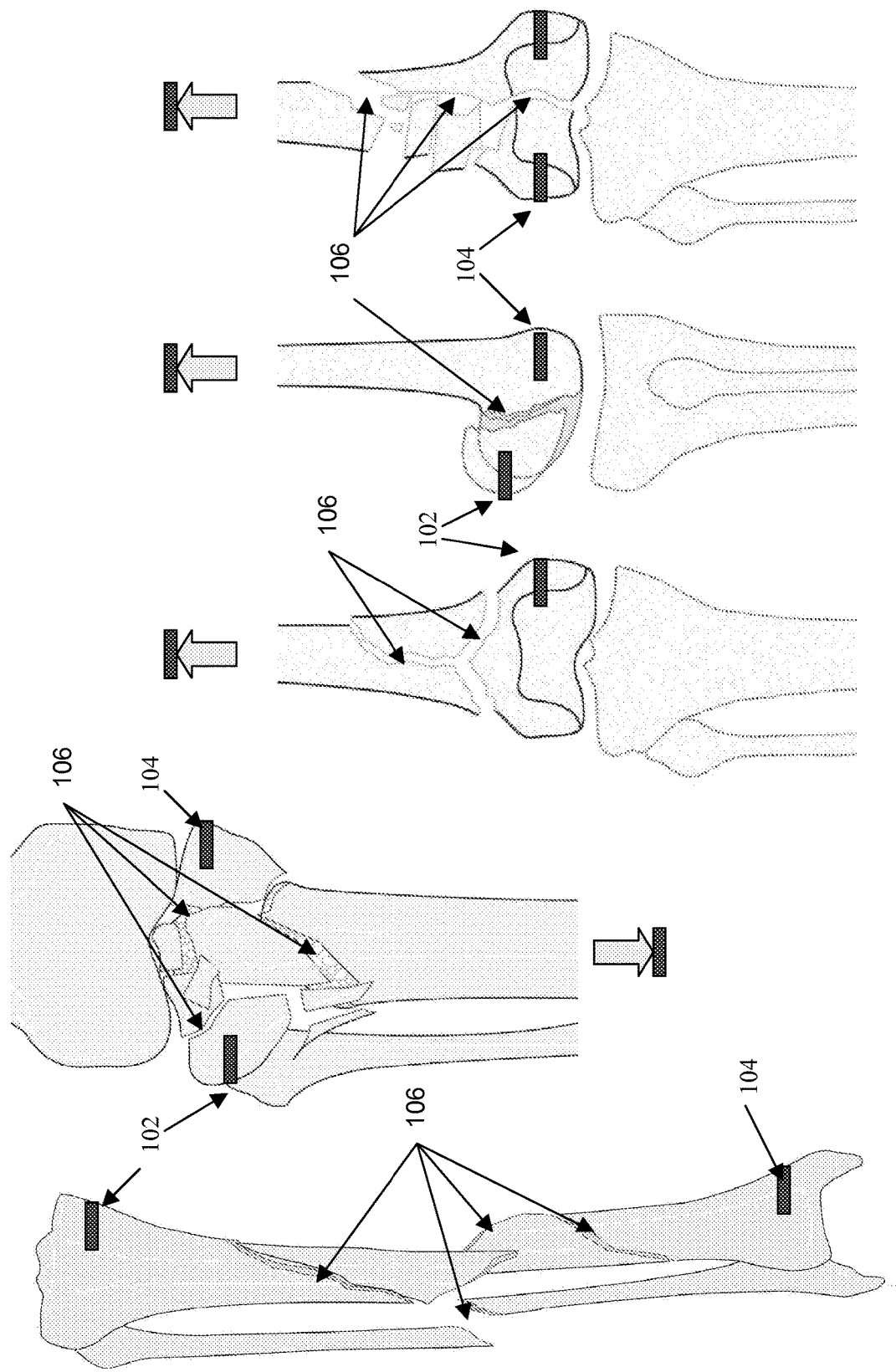
FIG. 18 illustrates exemplary marker placements.

As shown in FIGS. 6-12, the system or method for performing bone or tissue manipulation may include implantation of at least one marker 102, 104 onto the fractured bone 100 on either side of the fracture 106. As best shown in FIG. 18 and as previously mentioned, the markers 102, 104 are preferably secured to the fractured bone on either side of the fracture as close as possible to the bone ends opposite the fracture 106. Moreover, as shown, for complex fractures, a marker 102, 104 may be placed only on the far ends of the fractured bone 100 being reduced. Alternatively, however, a marker 102, 104 may be installed on each or most of the bone fragments.

Next, an image of the fractured bone 100 may be acquired using, for example, an x-ray 110 or any other suitable imaging device such as but not limited to 3D x-ray, a computed tomography (CT) scan, a magnetic resonance imaging (MRI), an ultrasound, etc.

Once the image of the fractured bone 100 has been obtained, the image may be merged with the orientation data obtained from the markers 102, 104 via, for example, the detection device 114. Preferably, the image of the fractured bone 100 may be overlapped and/or calibrated with the orientation data obtained by, for example, the detection device 114, so that the orientation of each markers 102, 104 is accurately reflected relative to each other at the time the image was captured.

Figure 21:
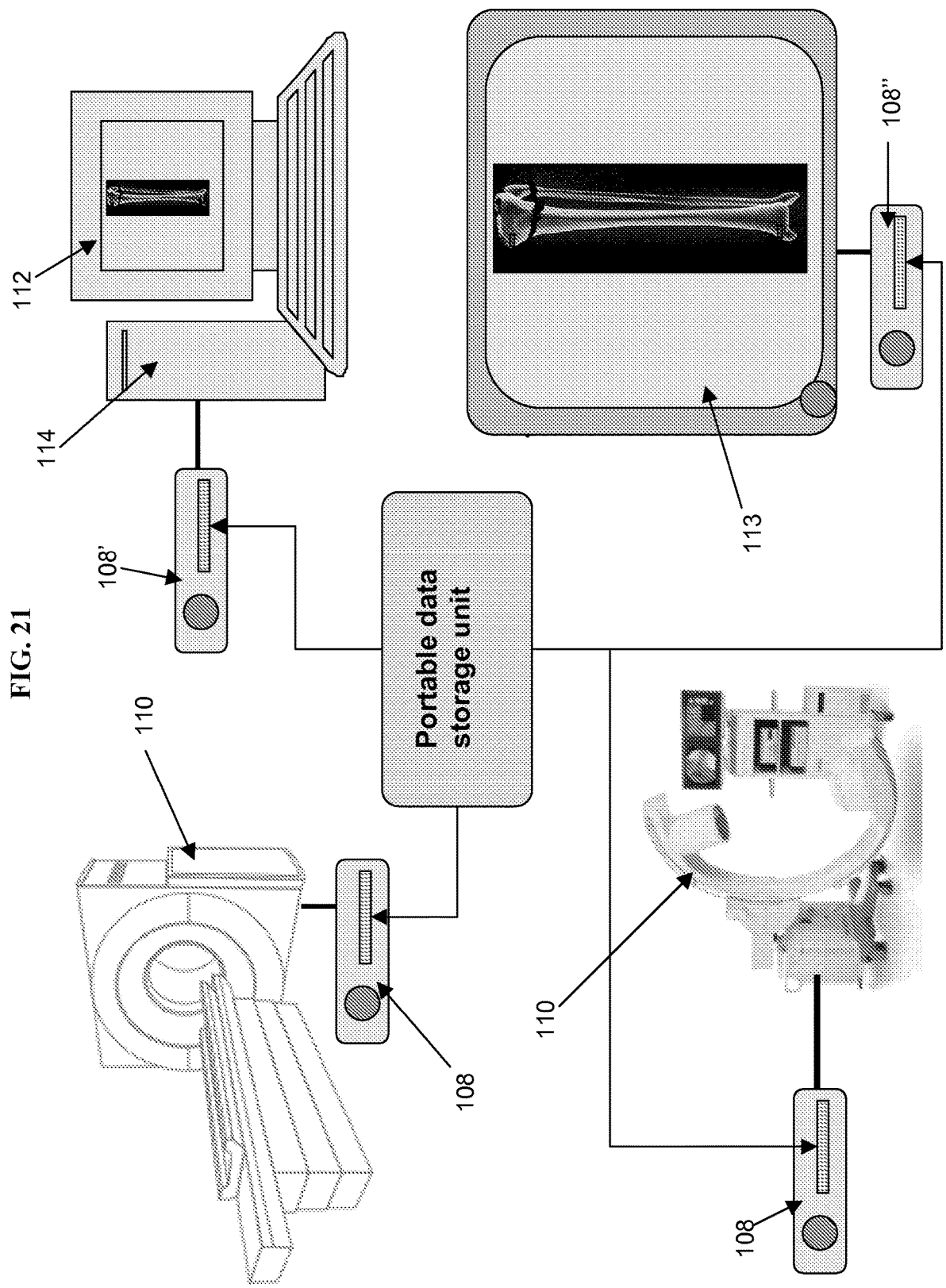
FIG. 21 illustrates the use of a portable data storage according to one aspect of the exemplary embodiment of the method for performing bone or tissue manipulation.
Figure 22:
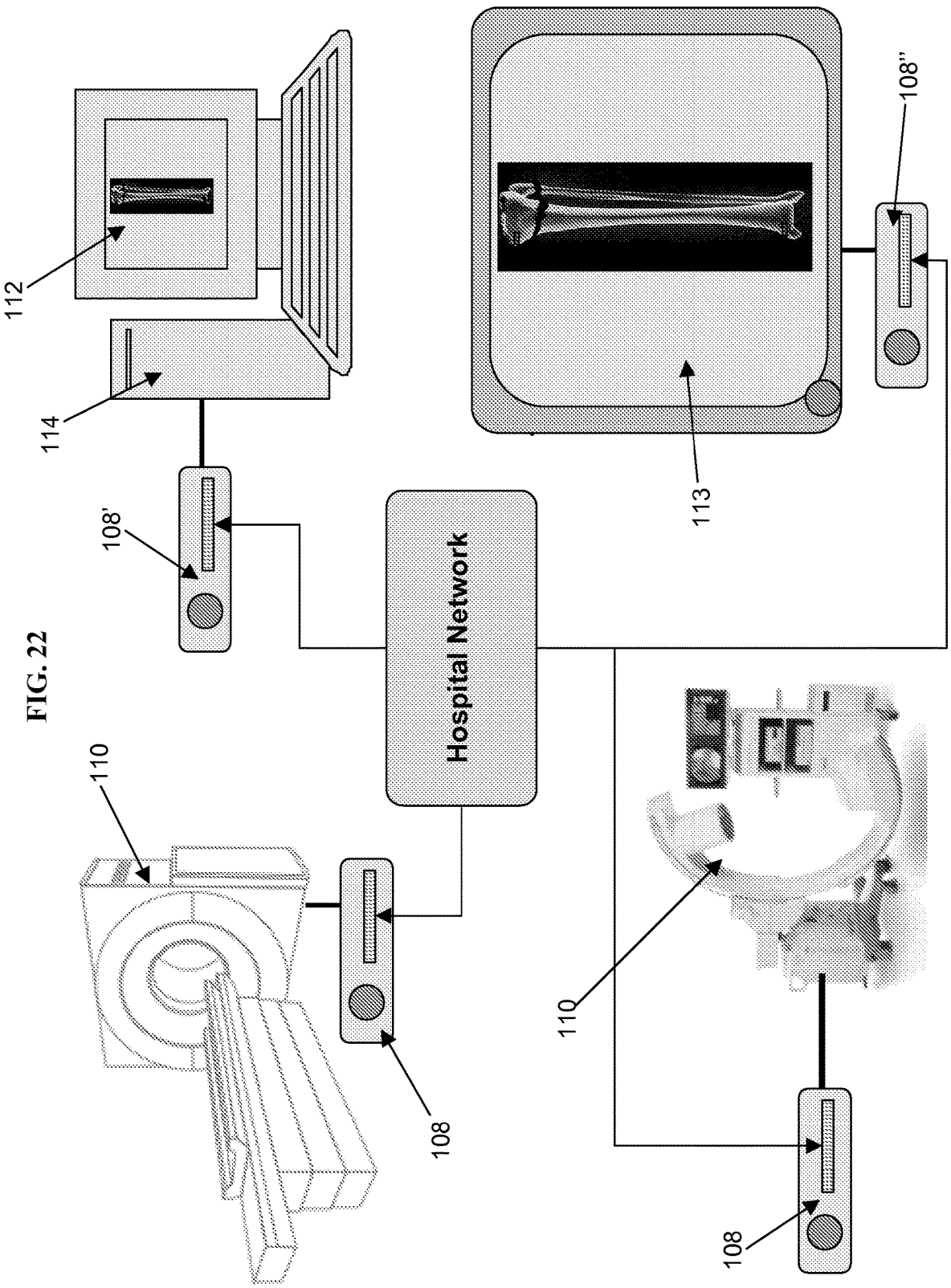
FIG. 22 illustrates the use of a hospital network according to another aspect of the exemplary embodiment of the method for performing bone or tissue manipulation.

Next, the pre-operative fracture reduction of the image may be preferably performed by the doctor and/or surgeon, aided by the image of the fractured bone displayed on, for example, a computer monitor 112, which may be based on the bone images and marker orientation. The virtual or simulated fracture reduction may be software based or any other means. After the virtual or simulated fracture reduction is completed, the data regarding the desired orientation of the markers 102, 104 may be stored in, for example, the detection device 114. Alternatively and/or in addition, the data regarding the desired orientation of the markers 102, 104 may be stored in one or more marker transponder or receivers, the markers themselves, or any other storage unit known in the art, such as, for example, a portable data storage unit as shown in FIG. 21, a hospital network as shown in FIG. 22, etc. so that the data can be used as a reference for the actual physical intra-operative fracture reduction. That is, for example, the detection device 114 may be programmed with the desired restored orientation of the bone fragments. During intra-operative fracture reduction, and based on the pre-operative virtual or simulated manipulation of the bone fragments, the system and method is preferably capable of automatically recognizing the actual orientation of the markers 102, 104 as they are being manipulated so that, for example, the detection device 114 can inform the doctor and/or surgeon via an indicator signal when the bone fracture has been properly reduced to the desired restored orientation. Alternatively and/or in addition, as previously mentioned, the marker transponder or receiver and/or the markers themselves may be programmed with the desired restored orientation of the bone fragments. Moreover, the marker transponder or receiver and/or the markers themselves may be capable of producing the indicator signal when the bone fracture has been properly reduced to the desired restored orientation. Alternatively and/or in addition, the method of performing bone or tissue manipulation may include an indicator device for transmitting the indicator signal.

Moreover, during intra-operative fracture reduction, the manipulation and orientation of the markers and hence of the bone fragments, may be continuously tracked and displayed in real time on a monitor 113 to aid the doctor and/or surgeon in reducing the fracture to the appropriate orientation. Once the desired restored orientation has been achieved, fixation of the fractured bone may be completed and reconfirmation and/or monitoring of the fracture can be performed with the aid of the image displayed on the monitor 113.

Figure 13:
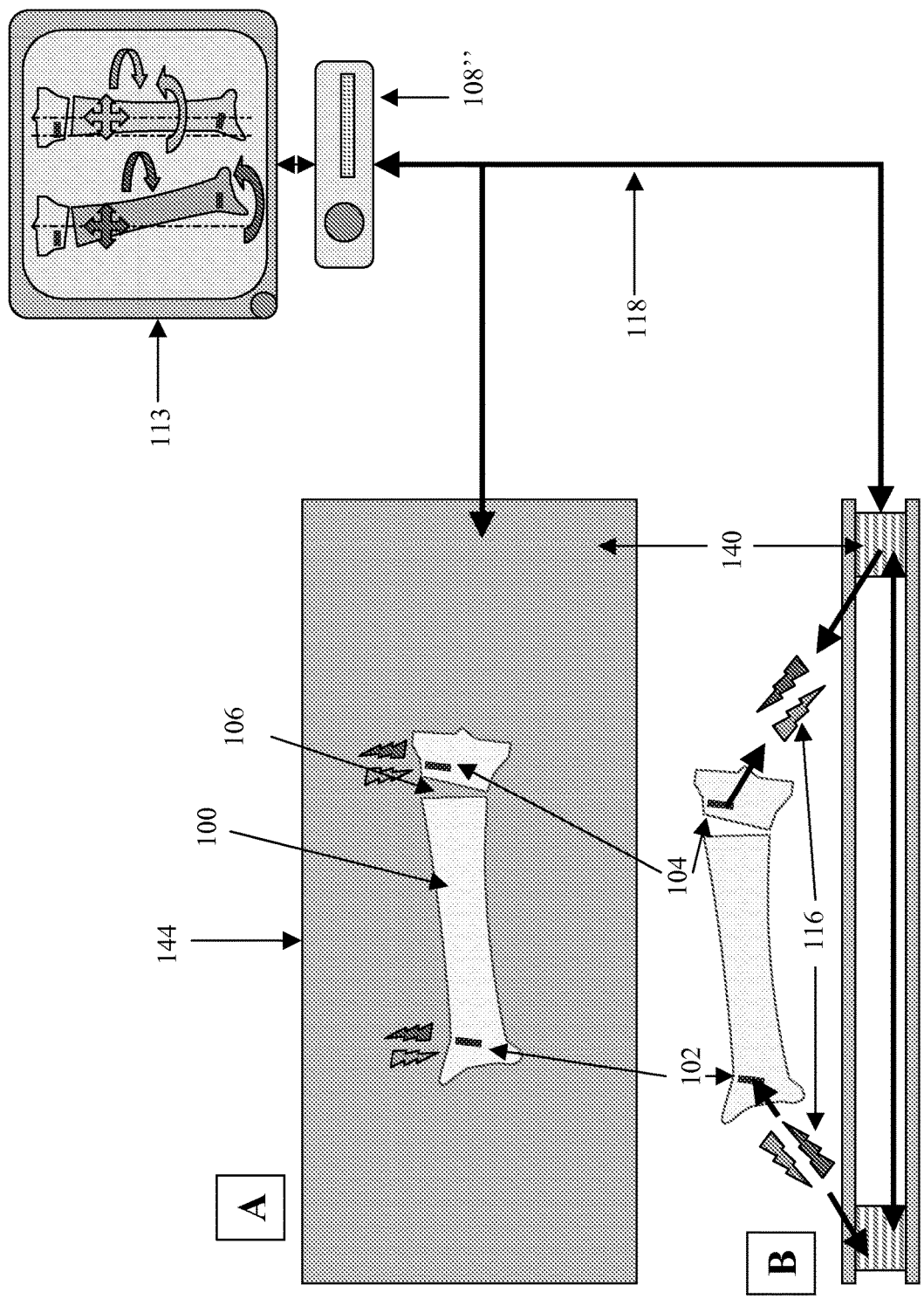
FIG. 13 illustrates a top and cross-sectional view of a signal receiving and/or transmitting platform.

In addition to or alternatively from the detection device 114, as shown in FIG. 13, the system and method for performing and optionally verifying bone or tissue manipulation may include a signal receiving and/or transmitting platform 144. The signal receiving and/or transmitting platform 144 may be in the form of a table, a frame, a board, a bed or any other support system that will accommodate the fractured bone 100 so that the markers 102, 104 can be monitored via the signal receiving and/or transmitting platform 144. The signal receiving and/or transmitting platform 144 may include one or more sensors 140 capable of detecting the orientation of the markers 102, 104.

Figure 14:
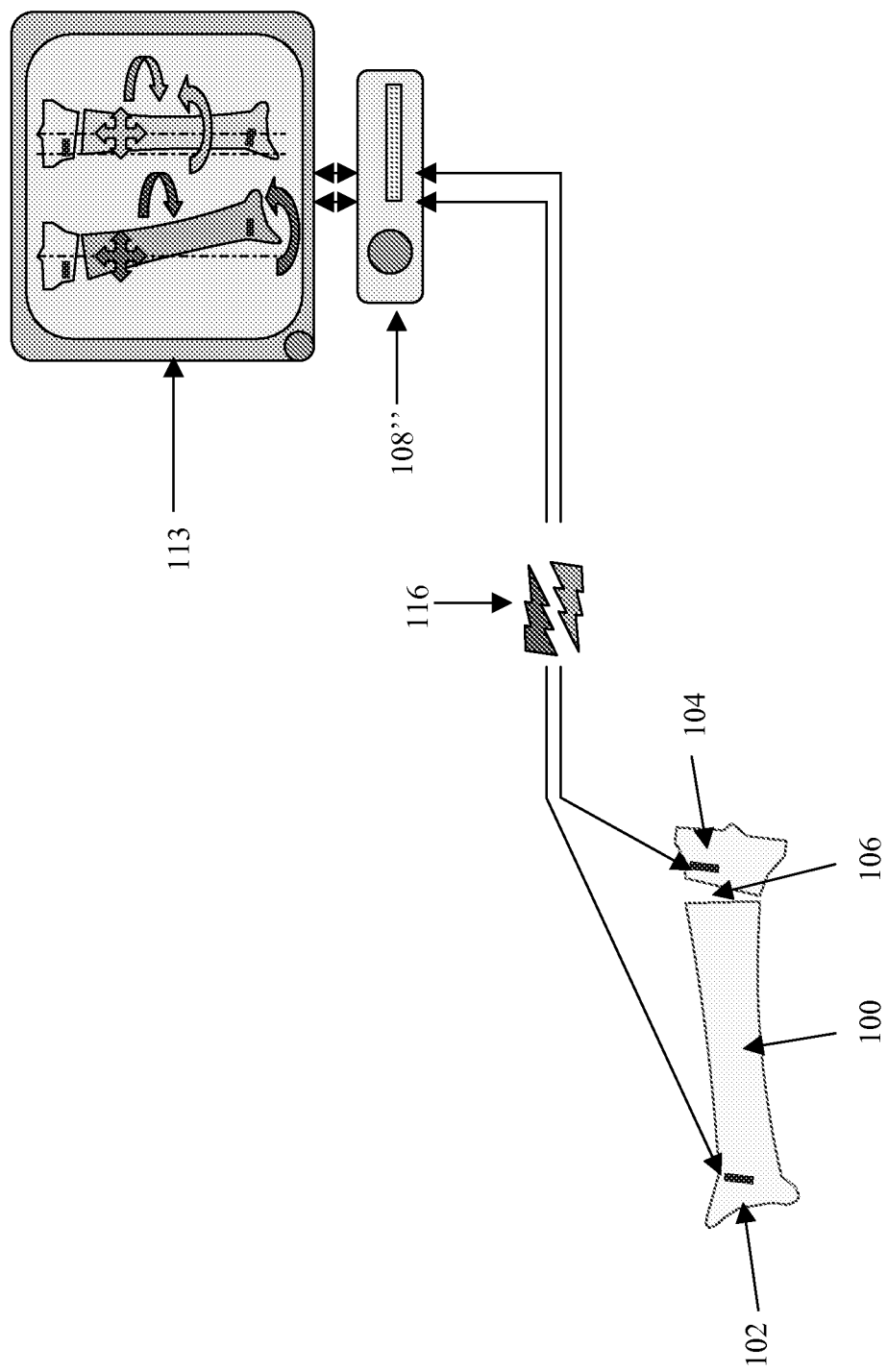
FIG. 14 illustrates one exemplary method for transmitting the signal in accordance with one exemplary embodiment of the method for performing bone or tissue manipulation.

As previously mentioned and as best shown in FIG. 14, the system and method for performing and optionally verifying bone or tissue manipulation preferably detects and preferably transmits signals containing the data on the orientation of the markers 102, 104 wirelessly 116. The wireless signal 116 may be received and/or transmitted by the various marker transponder or receivers 108. The wireless signal 116 may then be displayed on monitors 113.

Figure 15:
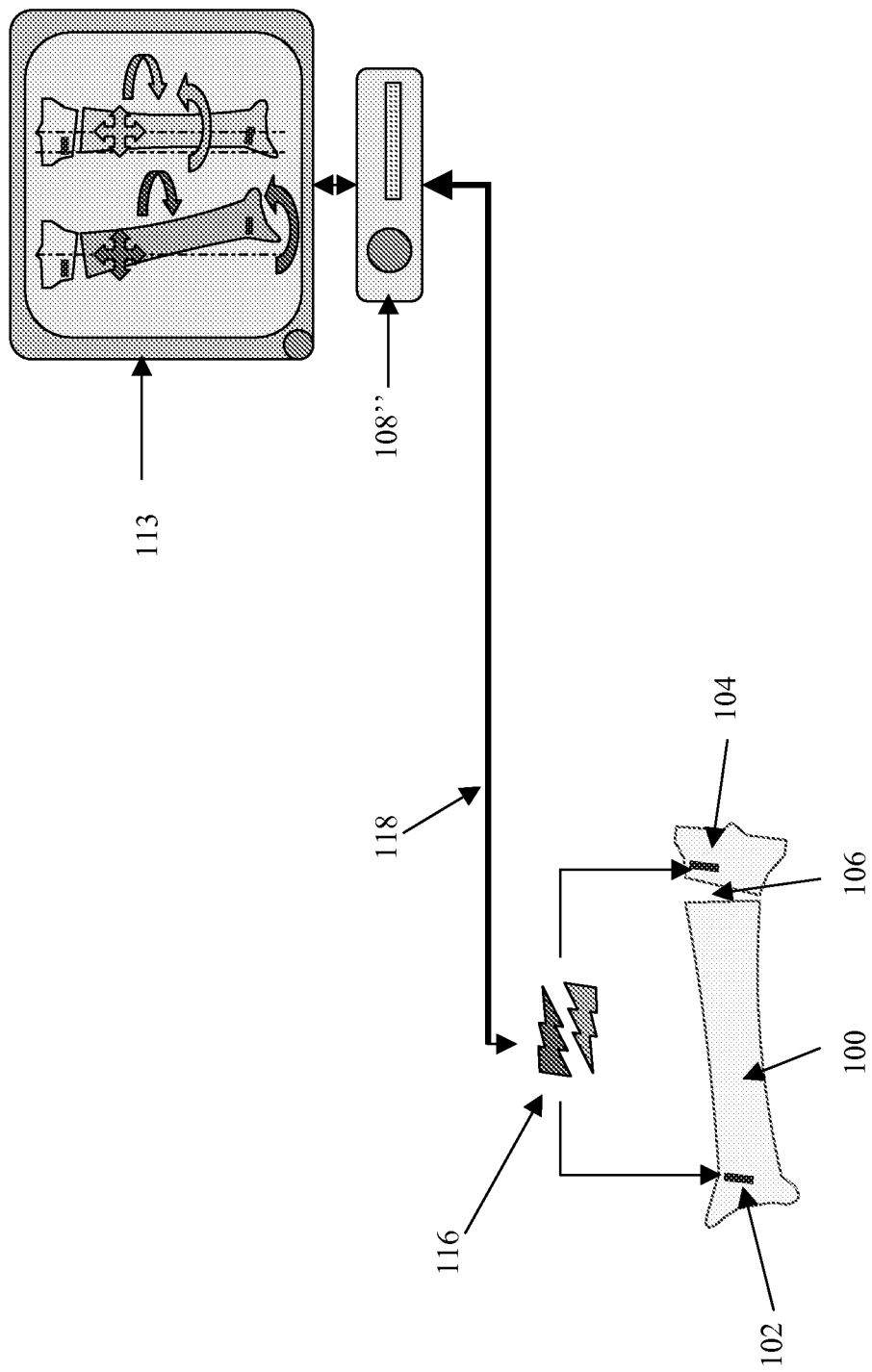
FIG. 15 illustrates another exemplary method for transmitting the signal in accordance with another exemplary embodiment of the method for performing bone or tissue manipulation.
Figure 16:
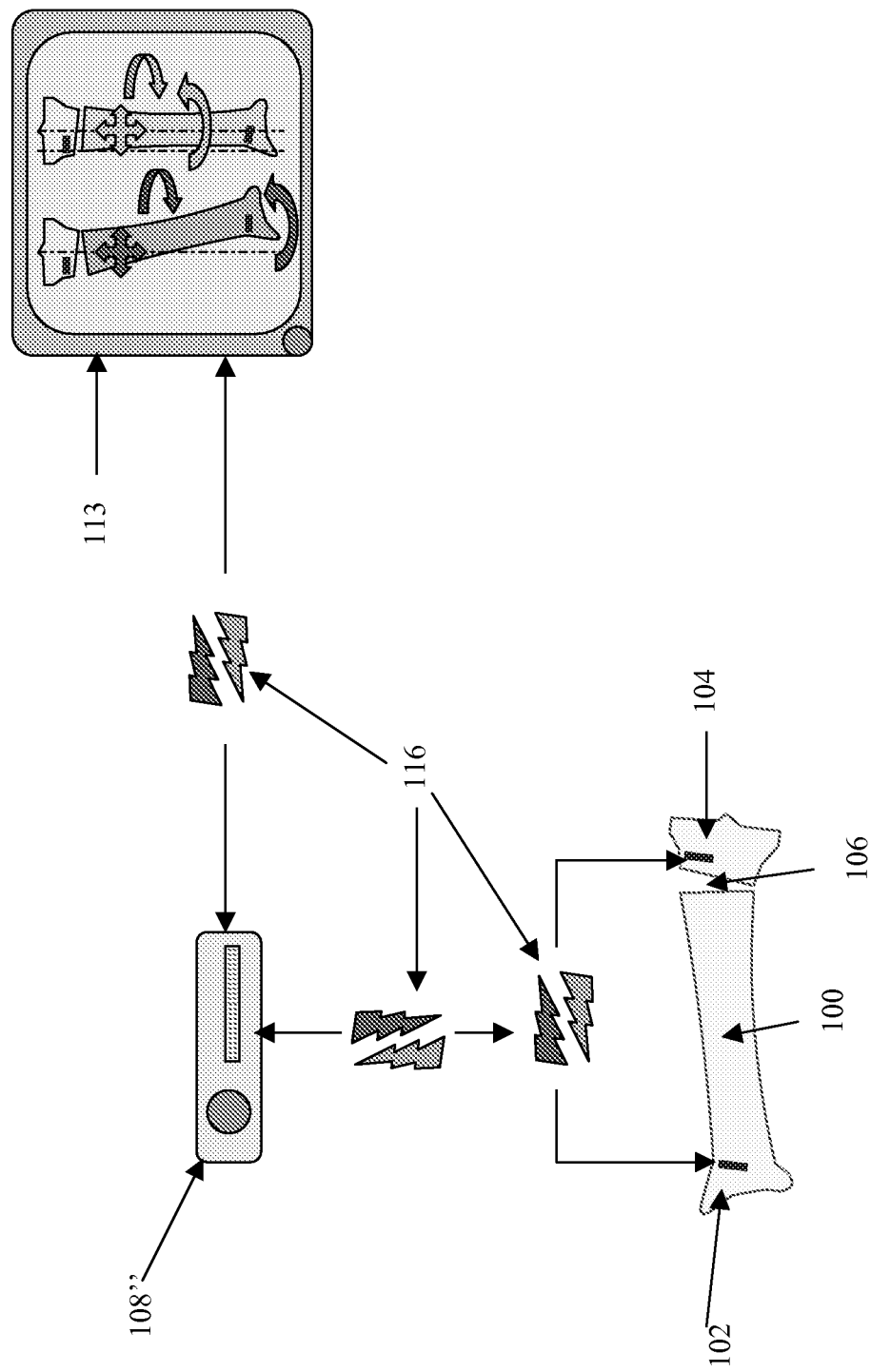
FIG. 16 illustrates another exemplary method for transmitting the signal in accordance with another exemplary embodiment of the method for performing bone or tissue manipulation.

Alternatively and/or in addition, as best shown in FIGS. 15 and 16, and as previously mentioned, the markers 102, 104 may be capable of both transmitting signals and/or receiving signals so that the markers 102, 104 can directly exchange signals regarding their orientation with respect to one another. The markers 102, 104 are also preferably capable of transmitting signals to one or more marker transponder or receivers 108. The signals may then be transmitted to, for example, the detection device, a display unit (e.g. a monitor), etc. The signals may then be transmitted by any means known in the art including by way of wires 118, wirelessly 116, etc. In the embodiment where the signals are transmitted via a wire 118, the markers 102, 104 may include a wire that exits the patient through the stab incisions and which connects to, for example, the detection device (e.g. computer console), enabling both communication between the markers 102, 104, as well as communication between the markers 102, 104 and the detection device used to alert the surgeon that a desired restored orientation has been achieved.

Figure 17:
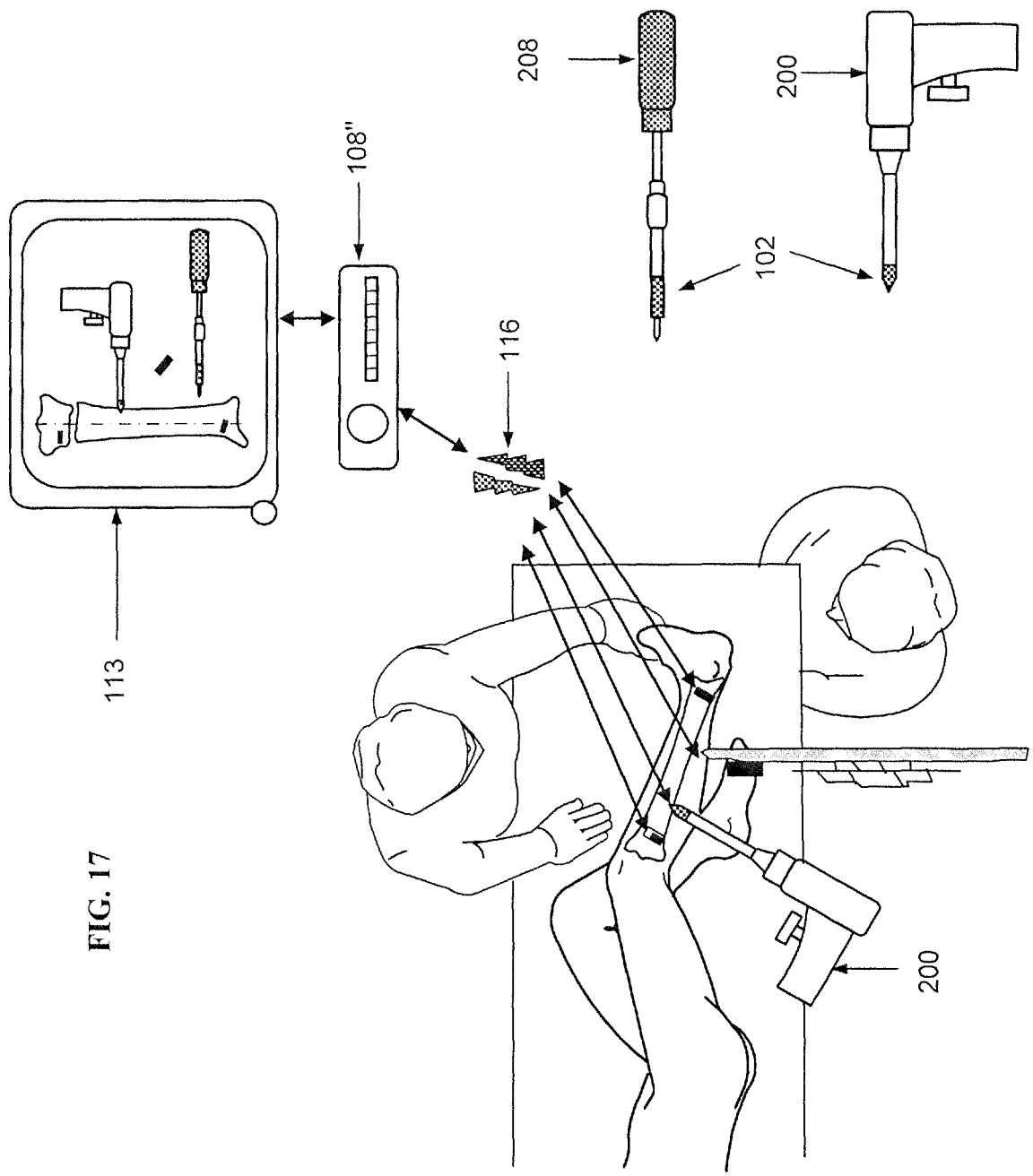
FIG. 17 illustrates the incorporation of markers onto intra-operative surgical instruments and fixation devices/implants according to another aspect of the exemplary embodiment of the method for performing bone or tissue manipulation.

In addition, the marker technology may also be incorporated into surgical instruments and/or fixation devices/implants to help facilitate accurate placement of the surgical instruments and/or fixation devices/implants. As shown in FIG. 17, in addition to fracture reduction, surgical instruments 200 and/or surgical implants 208 can be equipped with one or more markers 102. The surgical instruments 200 and/or fixation devices/implants 208 may then be navigated based on pre-operative determination of the desired restored orientation of the bone fragments. Similar to the markers used in connection with the reduction procedure, the surgical instrument and/or fixation device/implant marker can be calibrated and predefined to a specific instrument or implant.

Figure 19:
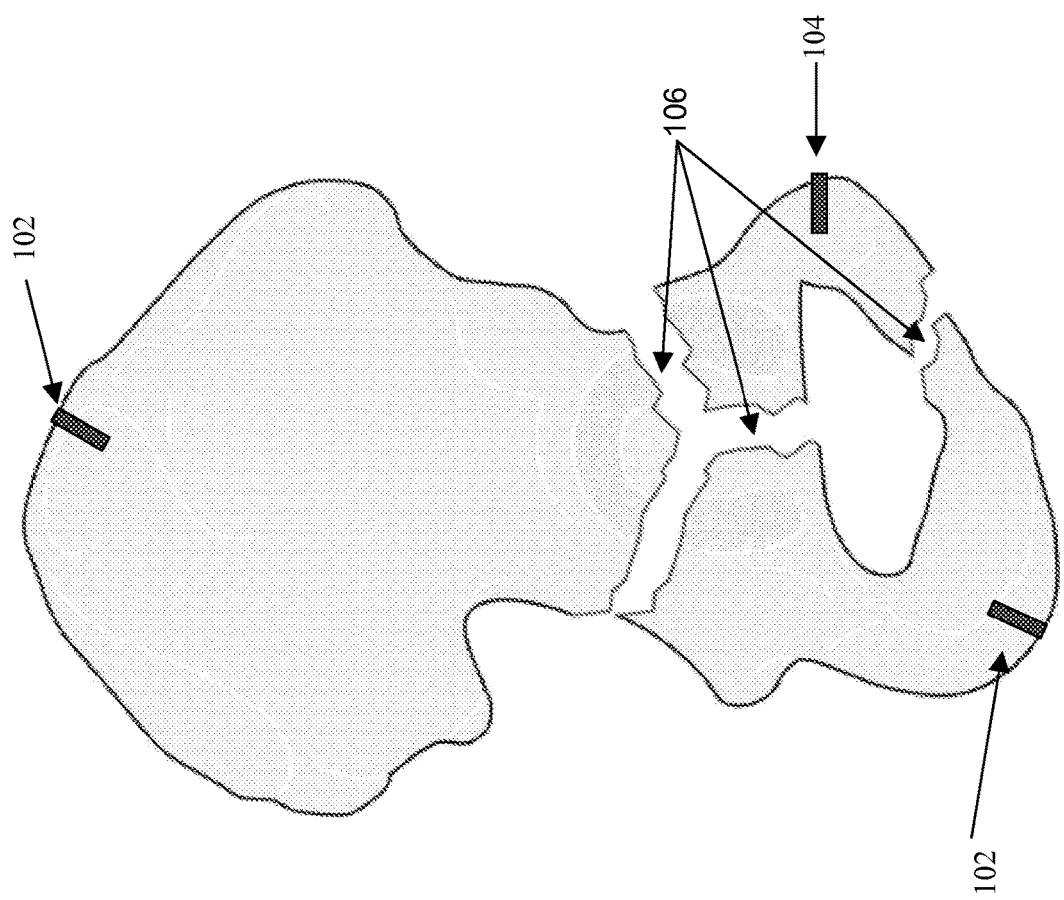
FIG. 19 illustrates exemplary marker placements.

Although the system and method for performing and optionally verifying bone or tissue manipulation has been described and may generally be used for fixation of the long bones, those skilled in the art will appreciate that the markers and system may be used for fixation of other parts of the body such as, for example, in the spine (as best shown in FIG. 19) for correction or movement of vertebra, for cranio-facial and mandible reconstruction (as best shown in FIG. 20), joints, bones in the hand, face, feet, extremities, etc. The system and method for performing and verifying fracture reduction may also be useful in complex fractures, such as for example, those shown in FIG. 18.

In addition, it should be understood that the embodiments described herein include not only pairs of markers, but also a system or a plurality of markers. This may be particularly useful for situations where multiple fragments are to be brought together or in the spine, where correction involves multiple, distinct vertebrae that require individual tracking. The system may allow for selective communication between the markers via channels or distinct frequencies.

It is foreseeable that the markers described herein can have many applications. For example, the markers may be applied on a short-term basis such as, for example, for no more than one or two days. Alternatively, the markers may be implanted for a long-term period. In this manner, the markers may be useful in monitoring the progress of deformity correction procedures where distraction osteogenesis takes place over a period of weeks or months. It is also conceivable that the markers could be used to provide biomechanical data related to the success of fracture healing. The markers could be used to develop a better understanding of the strain seen by a bone.

Alternatively, surgeons may prefer to use the markers in a more "on-the-fly" manner, without pre-op planning, or reliance on 3D imaging. In this case, the markers may be used to limit the patient's exposure to radiation by reducing the use of intra-operative fluoroscopy. The surgeon may implant the markers as described above and may take a perpendicular pair, for example an anterior/posterior view and a lateral view, of 2D images inclusive of the markers. The surgeon then "tags" or registers each marker to the 2D image of the bone fragment to which it is anchored, designating one bone fragment in the image to be stationary. As the reduction maneuver is being performed, the mobile 2D bone fragment representation moves on-screen in both views, tracking the motion that the markers communicate to the external signaling device such that the surgeon has an on-screen estimation of what the actual images would look like if they were taken live. In such an embodiment, the limb preferably is maintained absolutely stationary during imaging and tagging prior to any reduction maneuver. Further, in such an embodiment the imaging and tagging procedure may be repeated mid-reduction to get a refreshed true image if there is concern that the estimated image is inaccurate due to inadvertent motion during the capture and tagging procedure, or due to a rotational component of the reduction maneuver.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A method for performing tissue manipulation, comprising the steps of:
   implanting first and second markers on first and second portions of tissue, respectively;
   capturing an image of the first and second portions of tissue with the first and second markers attached thereto;
   merging the image with orientation data transmitted from the first and second markers;
   manipulating the image of the first and second portions of tissue in a simulated environment to a planned orientation;
   determining positions of the first and second markers in the planned orientation;
   programming a detection device with the planned orientation;
   determining, with the detection device, a current marker orientation, the detection device generating an indicator signal when the first and second markers are in the planned orientation;
   manipulating the first and second portions of tissue, until the indicator signal is generated by the detection device indicating the planned orientation has been substantially achieved; and
   after the planned orientation is achieved, implanting a fixation device to fix the first and second portions of tissue in the planned orientation.

2. The method of claim 1, wherein the detection device is one of a computer console, x-ray machine, computed tomography scan and a receiver.

3. The method of claim 1, wherein the first portion of tissue is a vertebra.

4. The method of claim 1, wherein the first and second markers wirelessly communicate with the detection device to determine marker orientation.

5. The method of claim 1, wherein the first and second markers are configured to communicate with one another.

6. The method of claim 5, wherein the communication between the first and second markers is continuous during the tissue manipulation.

7. The method of claim 1, further comprising:
   displaying the indicator signal on a display.

8. The method of claim 1, wherein the image is merged with the orientation data via the detection device.

9. The method of claim 1, wherein the image and the orientation data are merged by one of overlapping and calibrating the image with the orientation data via the detection device so that the orientation of the first and second markers is reflected relative to each other at the time the image was captured.

* * * * *